(12) United States Patent
Gylleby et al.

(10) Patent No.: US 10,300,208 B2
(45) Date of Patent: May 28, 2019

(54) MEDICAMENT DELIVERY DEVICE WITH DELIVERY FINISH SIGNAL DELAY

(71) Applicant: CAREBAY EUROPE LTD, Sliema (MT)

(72) Inventors: Stefan Gylleby, Stockholm (SE); Daniel Sall, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 343 days.

(21) Appl. No.: 15/312,239

(22) PCT Filed: May 5, 2015

(86) PCT No.: PCT/EP2015/059843
§ 371 (c)(1),
(2) Date: Nov. 18, 2016

(87) PCT Pub. No.: WO2015/185311
PCT Pub. Date: Dec. 10, 2015

(65) Prior Publication Data

US 2017/0087304 A1    Mar. 30, 2017

(30) Foreign Application Priority Data

Jun. 5, 2014  (SE) ..................................... 1450684

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/31581* (2013.01);
(Continued)

(58) Field of Classification Search
CPC .............. A61M 5/3157; A61M 5/2033; A61M 5/31581; A61M 5/46; A61M 2005/202;
(Continued)

(56) References Cited

U.S. PATENT DOCUMENTS

| 8,414,533 B2 | 4/2013 | Alexandersson |
| 2013/0041324 A1 | 2/2013 | Daniel |

(Continued)

FOREIGN PATENT DOCUMENTS

| EP | 2583705 A1 | 4/2013 |
| EP | 2698179 A1 | 2/2014 |

(Continued)

OTHER PUBLICATIONS

WO2011/123024; Daniel; date of publication: Oct. 6, 2011; Priority data: Mar. 31, 2010. (Year: 2011).*

(Continued)

*Primary Examiner* — Manuel A Mendez
(74) *Attorney, Agent, or Firm* — McDonnell Boehnen Hulbert & Berghoff LLP

(57) ABSTRACT

A medicament delivery device is presented having a housing with a distal and a proximal end, the housing being adapted to receive a medicament container with a delivery member or with a connectable delivery member for delivery of a medicament. The device also has a drive mechanism arranged to act on a plunger rod, which plunger rod in turn is arranged to act on the medicament container for providing automatic delivery of the medicament and a hold-release mechanism interactively connected to the drive mechanism for releasing the drive mechanism from a biased position. A delayable signal generating mechanism generates an audible and/or tactile and/or visual signal indicating that the medicament has been completely delivered, which delayable (Continued)

signal generating mechanism is operably connected between said pre-tensioned drive mechanism and said plunger rod.

20 Claims, 20 Drawing Sheets

(51) Int. Cl.
*A61M 5/46* (2006.01)
*A61M 5/31* (2006.01)

(52) U.S. Cl.
CPC ......... *A61M 5/46* (2013.01); *A61M 2005/202* (2013.01); *A61M 2005/206* (2013.01); *A61M 2005/208* (2013.01); *A61M 2005/3125* (2013.01); *A61M 2005/3126* (2013.01); *A61M 2005/3143* (2013.01); *A61M 2205/581* (2013.01); *A61M 2205/582* (2013.01); *A61M 2205/583* (2013.01)

(58) Field of Classification Search
CPC ...... A61M 2005/206; A61M 2005/208; A61M 2005/3125; A61M 2005/3126; A61M 2005/3143; A61M 2205/581; A61M 2205/582; A61M 2205/583; A61M 5/20; A61M 5/1456; A61M 5/1452; A61M 5/5086; F04B 27/1804

USPC ........................................................ 604/189
See application file for complete search history.

(56) References Cited

U.S. PATENT DOCUMENTS

2013/0218093 A1    8/2013  Markussen et al.
2015/0209517 A1*   7/2015  Brunnberg .......... A61M 5/2033
                                              604/198

FOREIGN PATENT DOCUMENTS

TW       201408344 A     3/2014
WO       2011/043714 A1  4/2011
WO       2012/117252 A1  9/2012
WO       2012/173553 A1  12/2012
WO       2013/178512 A1  12/2013

OTHER PUBLICATIONS

WO2012/025639; Markussen; date of publication: Mar. 1, 2012; Priority data: Aug. 31, 2010. (Year: 2012).*
WO2013/178512, Brunnburg et al., date of publication: Dec. 5, 2013, priority data: May 31, 2012. (Year: 2013).*
International Search Report and Written Opinion for Int. App. No. PCT/EP2015/059843, dated Aug. 20, 2015.

* cited by examiner

MEDICAMENT DELIVERY DEVICE WITH DELIVERY FINISH SIGNAL DELAY

CROSS REFERENCE TO RELATED APPLICATIONS

The present application is a U.S. National Phase Application pursuant to 35 U.S.C. § 371 of International Application No. PCT/EP2015/059843 filed May 5, 2015, which claims priority to Swedish Patent Application No. 1450684-4 filed Jun. 5, 2014. The entire disclosure contents of these applications are herewith incorporated by reference into the present application.

TECHNICAL FIELD

The present invention relates to a medicament delivery device and in particular a device capable of indicating to a user when a medicament delivery sequence has been completed such that it is safe to remove the device from the dose delivery site.

BACKGROUND

Many medicament delivery devices are developed for self-administration, i.e. a user performs the medicament delivery her-, or himself. This requires a medicament delivery device, which is reliable, accurate, safe and easy to use. In order to meet these requirements, the risk of human errors must be minimized, the number of actions needed to be performed in order to receive a dose need to be reduced and the device must be intuitive to use. Thus, in order to minimize the risk of human errors, it is desirable to have a device that accurately provides a user with confirmation that he/she has received a complete dose of medicament.

Medicament delivery devices such as injection devices providing automatic or manual delivery member insertion, automatic injection of a medicament, automatic delivery member retraction or automatic covering of the delivery member are known in the art. Though these injection devices known in the art have a major number of advantages, there is always room for improvement. For example, a device that provides both a complete delivery of medicament and release of a member that produces a reliable audible and/or tactile and/or visible confirmation to the user that the delivery has been completed has hitherto been required to be manufactured to extremely tight tolerances.

For example, a release of a member that produces a reliable audible and/or tactile and/or visible confirmation to the user that the delivery has been completed is disclosed in WO2011043714A1. The release of a member that produces a reliable audible and/or tactile and/or visible confirmation to the user that the delivery has been completed is accomplished by disengaging a plunger rod from a second activator member once the plunger rod has terminated its displacement for delivering the medicament. The termination of the plunger rod displacement and the disengaging of the plunger rod from the second activator member must occur simultaneously if both a complete delivery of a medicament and a release of the second activator member which produces the reliable audible and/or tactile and/or visible confirmation to the user that the delivery has been completed are to be accomplished.

Thus, in WO2011043714A1 there is only one mechanical position that is used to activate the release of the second activation member at the point where it is expected that the plunger displacement will terminate. The precision of the timing of the termination of plunger displacement and disengagement of the plunger from the second activation member relies on the manufacturing and assembly dimensions of the parts of the device and thus the tolerances play an important role in the proper functioning of the device.

Thus, in order to compensate for component tolerances a signal generating member needs to be released before the plunger displacement has terminated. A user may then be prone to remove the device from the delivery site causing the medicament to not be completely delivery to the patient. In order to ensure a complete and accurate delivery of a medicament all the parts or components of the device must be manufactured to very tight tolerances leading to high manufacturing and assembling costs. Even the medicament container must be manufactured with such tight tolerances in mind, which is rare.

Thus, it would be an improvement in the art to provide a medicament delivery device that can be manufactured and assembled having reliable effects such as a complete delivery of a medicament followed by an audible and/or tactile and/or visible confirmation to the user that the delivery has been completed.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices. This aim is obtained by a medicament delivery device comprising the features of the independent patent claim 1. Preferable embodiments of the invention form the subject of the dependent patent claims.

According to the present invention, it comprises a medicament delivery device provided with a preferably elongated housing that has a distal and a proximal end. The housing comprises preferably a proximal housing part and a main housing part which are releasibly connected to each other.

The housing may be adapted to receive a medicament container with a delivery member. The delivery member may either be attached to or made integral with the medicament container or may be a connectable delivery member for delivery of a medicament. The connection elements may be of different type, like threads, bayonet connections or luer connections, for example.

The medicament delivery device may further preferably comprise a drive mechanism movable in said housing between biased and released positions and arranged to act on a plunger rod, where the plunger rod is arranged to act on the medicament container for providing automatic delivery of the medicament. The drive mechanism is preferably pre-tensioned/biased and will preferably interact with a hold-release mechanism. The hold-release mechanism is then interactively connected to the drive mechanism for holding the drive mechanism in the biased position and releasing the drive mechanism from the biased position. Further, the hold-release mechanism may on the one hand be automatically operated such that a pressing of the device against a dose delivery site will activate the drive mechanism. On the other hand, the hold-release mechanism may on the other hand be manually operated such that the user activates the drive mechanism by e.g. pressing a button or the like.

According to a preferable solution, the medicament delivery device may comprise a delayable signal generating mechanism for generating an audible and/or tactile and/or visual signal indicating that the medicament has been completely delivered. According to a favourable solution, the delayable signal generating mechanism may be operably connected between said drive mechanism and said plunger rod. Further, the delayable signal generating mechanism is releasably connected to the hold-release mechanism such that when the plunger rod nears or reaches the end of its operating stroke, the delayable signal generating mechanism is released from the hold-release mechanism whereby the delayable signal generating mechanism is enabled to interact with the drive mechanism for generating the audible and/or tactile and/or visual signal indicating that a medicament has been completely delivered. With this solution it is ensured that the user receives a positive indication that the dose delivery sequence has ended and that it is safe to remove the device from the dos delivery site. Because the delayable signal generating mechanism is placed between the drive mechanism and the plunger rod, the problem with tolerances is greatly reduced and also the number of components may be reduced in comparison to state of the art solutions.

According to a feasible solution, the delayable signal generating mechanism comprises a signal generating element and a delay element configured to be releasably connected to each other; and the drive mechanism comprises a plunger rod driver and a drive element for biasing the plunger rod driver towards the proximal end of the device. Moreover, the plunger rod driver (54) is preferably operably arranged to said plunger rod via said signal generating element.

According to a possible design solution, the signal generating element is connected to the plunger rod driver by a connection configured to restrict a rotational displacement but to allow an axial displacement between said signal generating element and said plunger rod driver, and the delay element is connected to said plunger rod driver by a connection configured to restrict an axial displacement but to allow a rotational displacement between said delay element and said plunger rod driver. Preferably, the connection between the delay element and the plunger driver is rotationally damped for regulating the rotational speed of said delay element. This may be particularly advantageous for delaying said generation of the audible and/or tactile and/or visual signal, since the signal generating element may be activated well after the end of the dose delivery sequence, thereby minimizing or avoiding the risk of removing the device prematurely.

According to a feasible solution, the hold-release mechanism comprises an activation member movable arranged in relation to the housing and having a locking element configured to releasably lock the plunger rod driver, and a blocking member movable arranged in relation to the activation member and configured to prevent the activation member to be actuated before the blocking member is actuated.

According to a possible design solution, the blocking member and the delay element are releasably connected to each other by first guide and hold elements configured to hold the delay element in a non-movable state in relation to the plunger driver when the plunger driver is locked by the locking element of the activation member and to guide the displacement of the delay element towards the proximal end of the device when the plunger driver is released by the activation member such that the displacement of the delay element is an axial displacement in relation to the blocking member.

According to a possible design solution, the delay element and the signal generating element are releasably connected to each other by second guide and hold elements configured:—to hold the signal generating element and said delay element in a non-displaceable state in relation to each other when the delay element together with the plunger driver are axially displaced in relation to the blocking member towards the proximal end of the device;—to promote a rotational displacement of the delay element in relation to the signal generating element when the delay element is released from the blocking member; and—to guide an axial displacement of the signal generating element in relation to the delay element towards the distal end of the device when the signal generating element is released from the delay element whereby the delay element together with the plunger driver continue to be axially displaced in relation to the blocking member towards the proximal end of the device such that a distal end surface of the signal generating element hits a proximal end surface of the plunger driver whereby the audible and/or tactile and/or visual signal indication that a medicament has been completely delivered is generated. Preferably, the rotational displacement of the delay element in relation to the signal generating element is rotationally damped by a viscous media arranged between the the delay element and the signal generating element.

This solution provides the possibility to control the rotational speed of the delay element in order to provide the desired delaying function in an easy and reliable way. Viscous media such as damping grease has the desired properties for slowing the rotation, thereby providing a delay.

According to a possible design solution, the second guide and hold elements comprise guide tracks and a central radially extending protrusion arranged on the outer circumferential surface of said signal generating element and a radial inwardly extending protrusion arranged on the inner circumferential surface of said delay member. The solution with guide tracks and protrusions provides possibilities of easy change of design and function as well as a robust construction with few components.

Further, the medicament delivery device may comprise a biased delivery member shield positioned at least partially and axially movable within the housing. The delivery member shield may then be operably connected to the hold-release mechanism in such a way that when the biased delivery member cover is pressed against a delivery site said hold-release mechanism is released. Thus, this safety feature prevents release of the device before the medicament delivery device is pressed against a dose delivery site such that a penetration is obtained.

The medicament delivery device also comprises a signal generating element spring arranged between a proximally directed end wall at the proximal end of the plunger rod driver and a distally directed surface of the circular end plate inside the signal generating element and configured to be compressed during medicament delivery.

According to a further design solution for allowing a resetting of the device, the medicament delivery member shield is interactively connected to the delay element by a connection configured to allow a rotation the delay element in relation to the signal generating element after the medicament has been delivered and the housing parts are rotated in relation to each other such that when the housing parts are separated the signal generating element is axially displaced towards the proximal end of the device by the force of the signal generating element spring. A possible design solution is where the medicament delivery member shield comprises elongated ledges on the inner surface of the the proximal housing part configured to interact with the radially extending ledges of the delay element.

Further, the drive mechanism is configured to be displaceable from the released position to the biased position by pushing on the plunger rod driver with a suitable tool in the distal direction causing the drive element to be tensioned until the locking element grips and holds the plunger rod driver. Also favourable solution is that the first guide and hold elements are configured to allow a rotation of the delay element in relation to the signal generating element when the plunger rod driver is displaced towards the distal end.

A possible design solution is wherein the first guide and hold elements comprise guide tracks arranged on inner surfaces of longitudinally extending arms of the blocking member and radially extending ledges arranged on the outer surface of the delay element; and also wherein the second guide and hold elements comprise guide tracks and a central radially extending protrusion arranged on the outer circumferential surface of said signal generating element and a radial inwardly extending protrusion arranged on the inner circumferential surface of said delay member These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION

Figure 1:
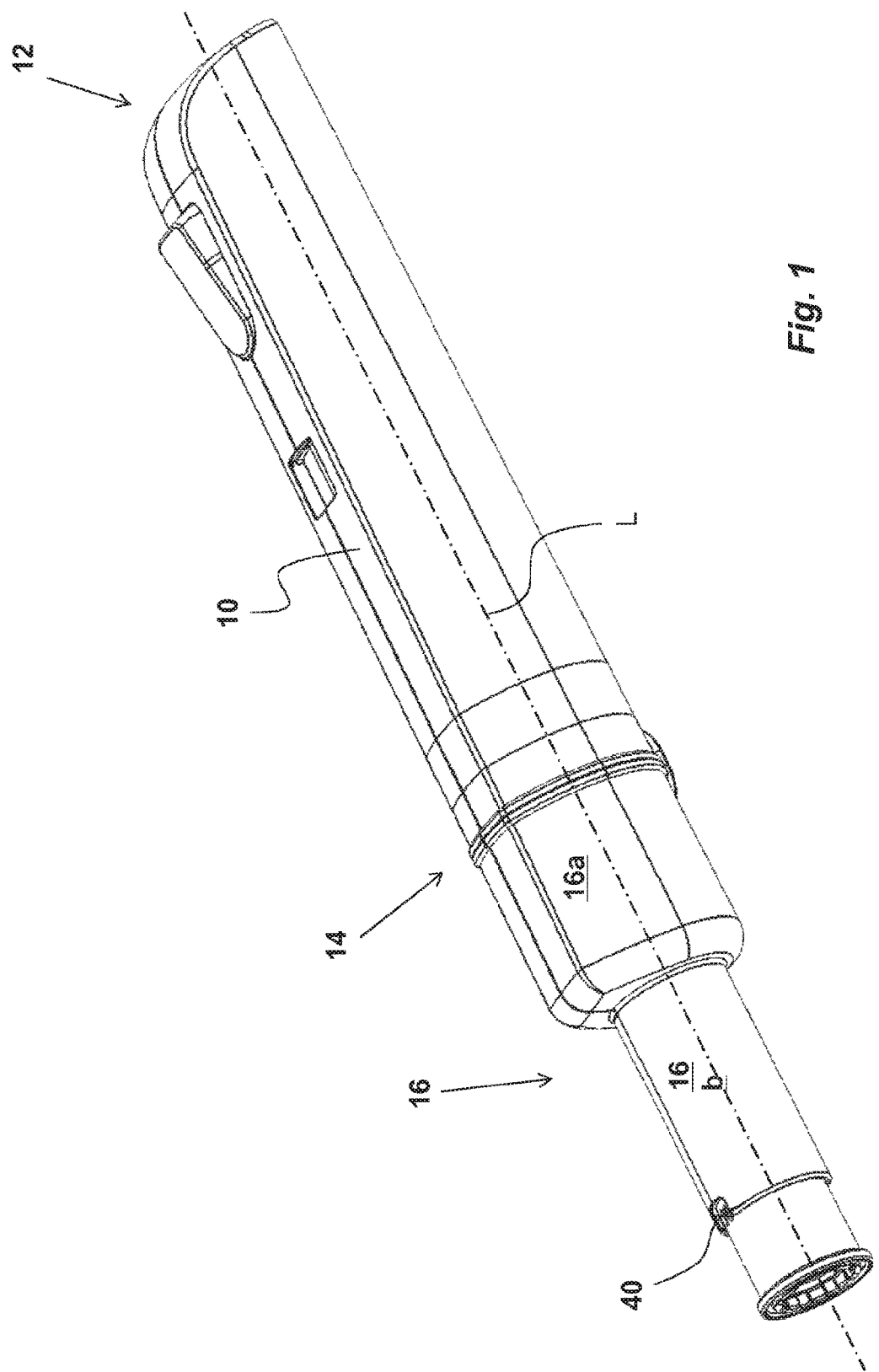
FIG. 1 shows a perspective view o a non-limiting embodiment of a medicament delivery device.
Figure 5:
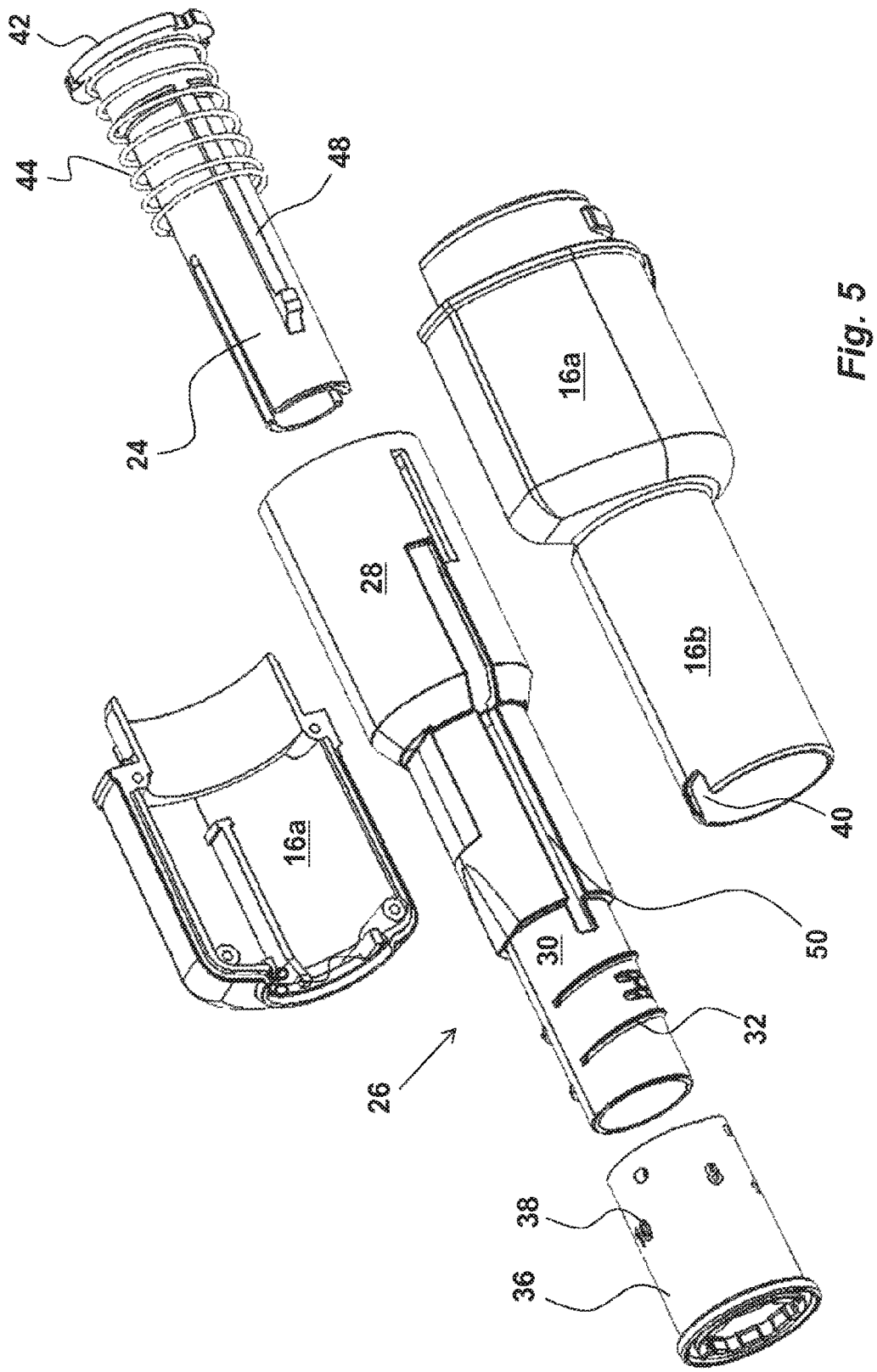
FIGS. 5-10 are detailed views of components comprised in the embodiment of FIG. 1, and FIGS. 11-20 are detailed views of the embodiment of FIG. 1, showing different functional states.

The embodiment shown in the drawings comprises a generally elongated main housing 10 having a distal end 12 and a proximal end 14, FIG. 1 and extending along a longitudinal axis L. At the proximal end 14 a proximal housing part 16 is arranged to be releasibly attached to a main housing part 10 with a first tubular part 16a, FIGS. 1 and 5, having generally the same diameter as the main housing 10. Attaching elements could comprise threads, bayonet connections, snap-in elements and the like. In the embodiment shown the attaching elements are bayonet connections, as will be described below. The first tubular part 16a is arranged to a second tubular part 16b having a lesser diameter than the first tubular part 16a. As seen in the embodiment of FIG. 5, the proximal housing part 16 is arranged in two halves. It is to be understood that other designs are feasible for the desired function and/or due to production aspects.

Figure 2:
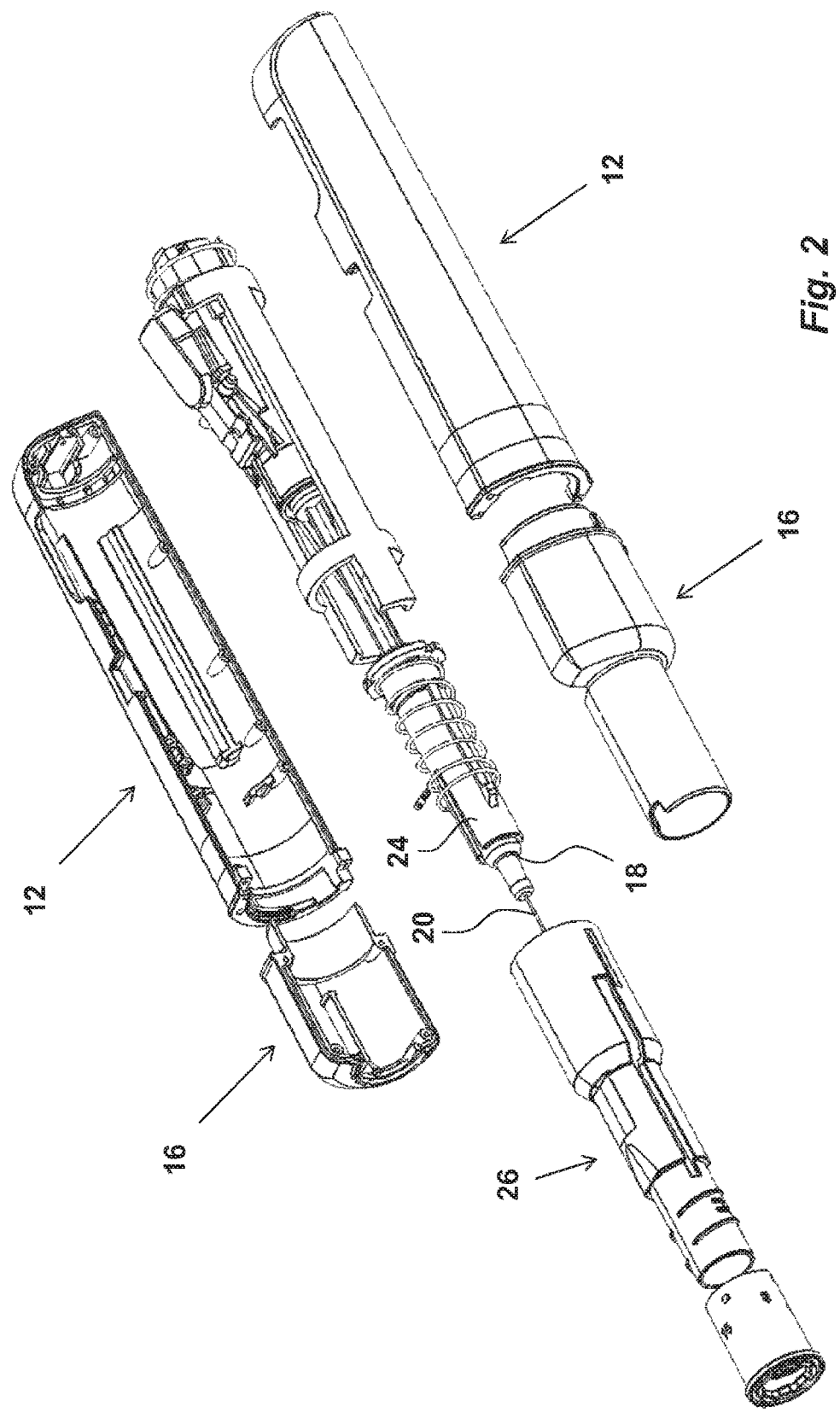
FIG. 2 is an exploded view of the embodiment of FIG. 1.
Figure 3:
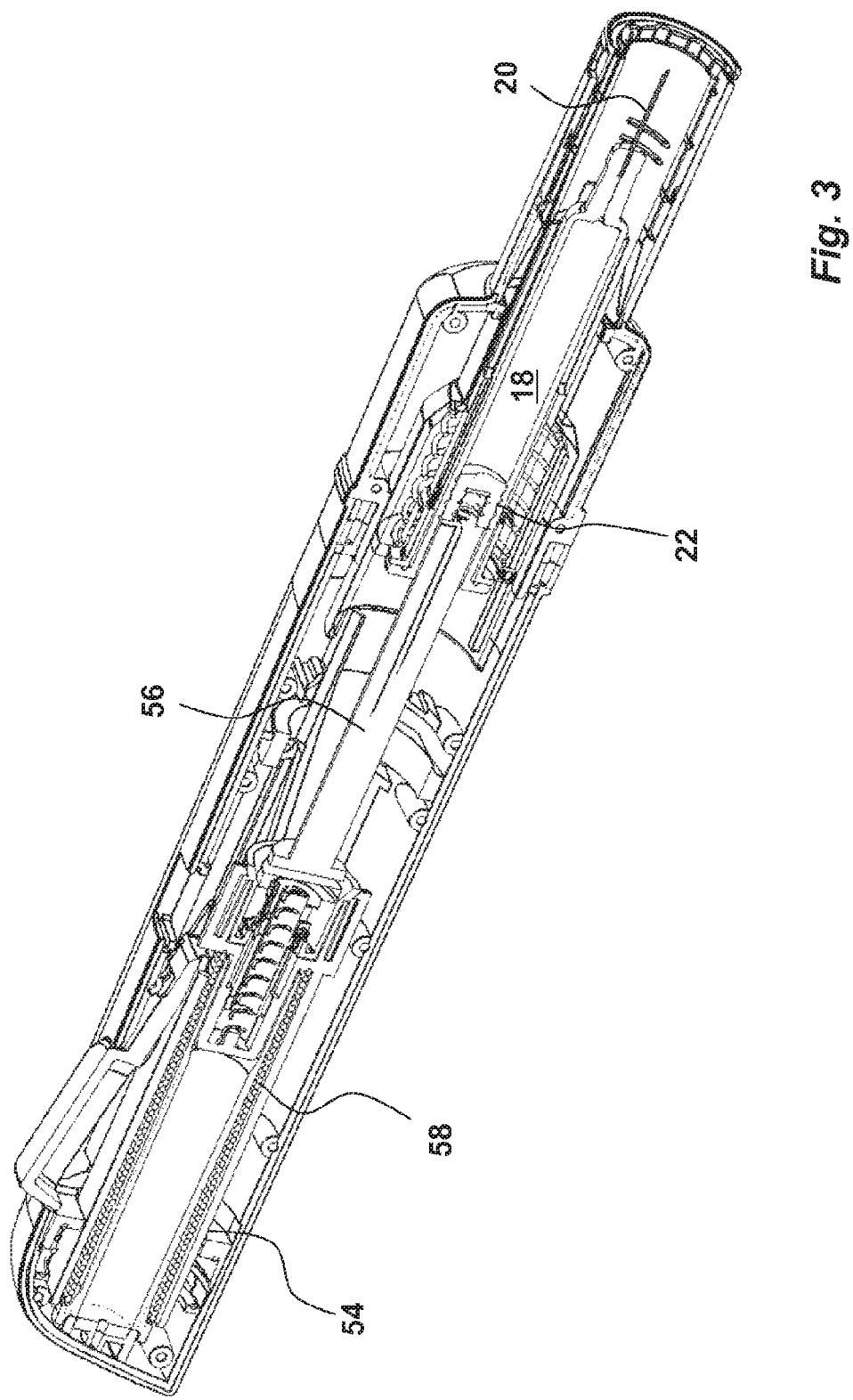
FIG. 3 is a cross-sectional longitudinal view of the embodiment of FIG. 1.

The proximal housing part 16 is designed to accommodate a medicament container 18, FIGS. 2 and 3. An appropriate medicament delivery member 20, FIGS. 2 and 3, is attached to, or made integral with, the medicament container 18. A movable stopper 22 is further arranged inside the medicament container, FIG. 3. The medicament container 18 is preferably arranged in a medicament container holder 24, FIGS. 2 and 5. The medicament container holder 24 is arranged to be slidable in the longitudinal direction as will be explained below.

Surrounding the medicament container holder 24 and coaxial therewith is a medicament delivery member shield 26, FIGS. 2 and 5. The medicament delivery member shield 26 is arranged with a distal tubular part 28, which transforms into a proximal tubular part 30, FIG. 5. In this respect, the inner diameter of the proximal tubular part 30 is somewhat larger than the outer diameter of the medicament container holder 24. Further, the outer diameter of the proximal tubular part 30 is somewhat smaller than the second tubular part 16b of the proximal housing part 16 such that the medicament delivery member shield 26 can move in the longitudinal direction in relation to the proximal housing part 16. The distal tubular part 28 of the medicament delivery member shield 26 is further arranged with an elongated ledge 31, FIG. 6, on its inner surface extending in the longitudinal direction, the function of which will be described below.

Figure 6:
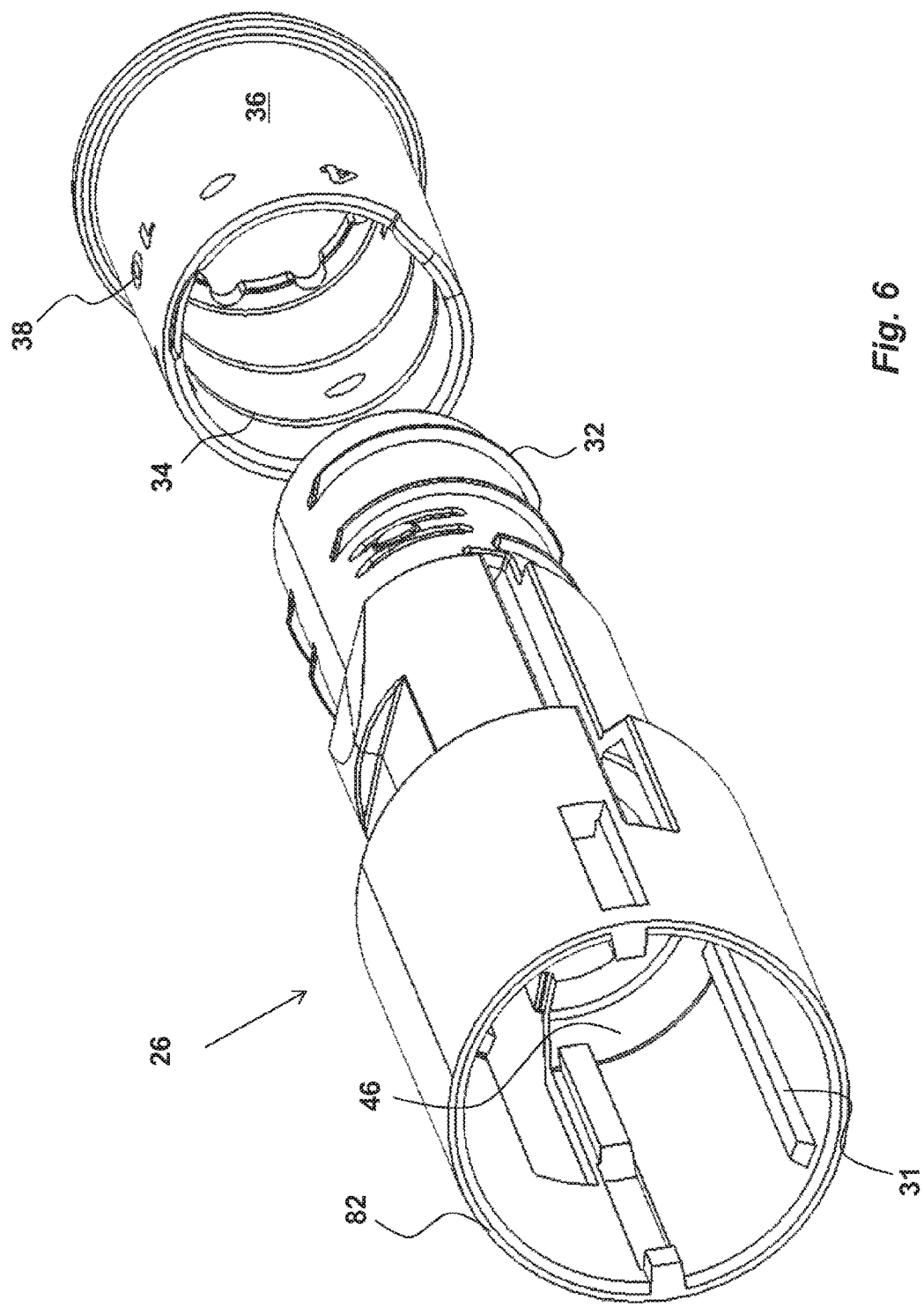

An outer surface of the medicament delivery member shield 26 is arranged with threads 32, FIGS. 5 and 6, which threads 32 are arranged to cooperate with corresponding threads 34, FIG. 6, on an inner surface of a generally tubular element 36, hereafter named depth adjuster. The outer surface of the depth adjuster 36 is arranged with indicia 38, such as numbers. These indicia 38 are to cooperate with a cut-out 40, FIGS. 1 and 5, in the proximal end of the second tubular part 16b.

The medicament container holder 24 is further arranged with a circumferential outwardly extending ledge 42 at its distal area, FIG. 5. A medicament delivery member return force element 44, in the embodiment shown preferably arranged as a compression spring, is arranged between a proximally directed surface of the ledge 42 and a distally directed circumferential ledge 46 of the medicament delivery member shield 26, FIG. 6, wherein the medicament delivery member return force element 44 urges the medicament container holder 24 and the medicament container 18 in the distal direction. The medicament holder 24 is also arranged with an outwardly directed ledge 48 on its outer surface, FIG. 5, which ledge 48 is intended to fit into a longitudinally extending groove 50 in the medicament delivery member shield 26 for guide purposes.

Figure 7:
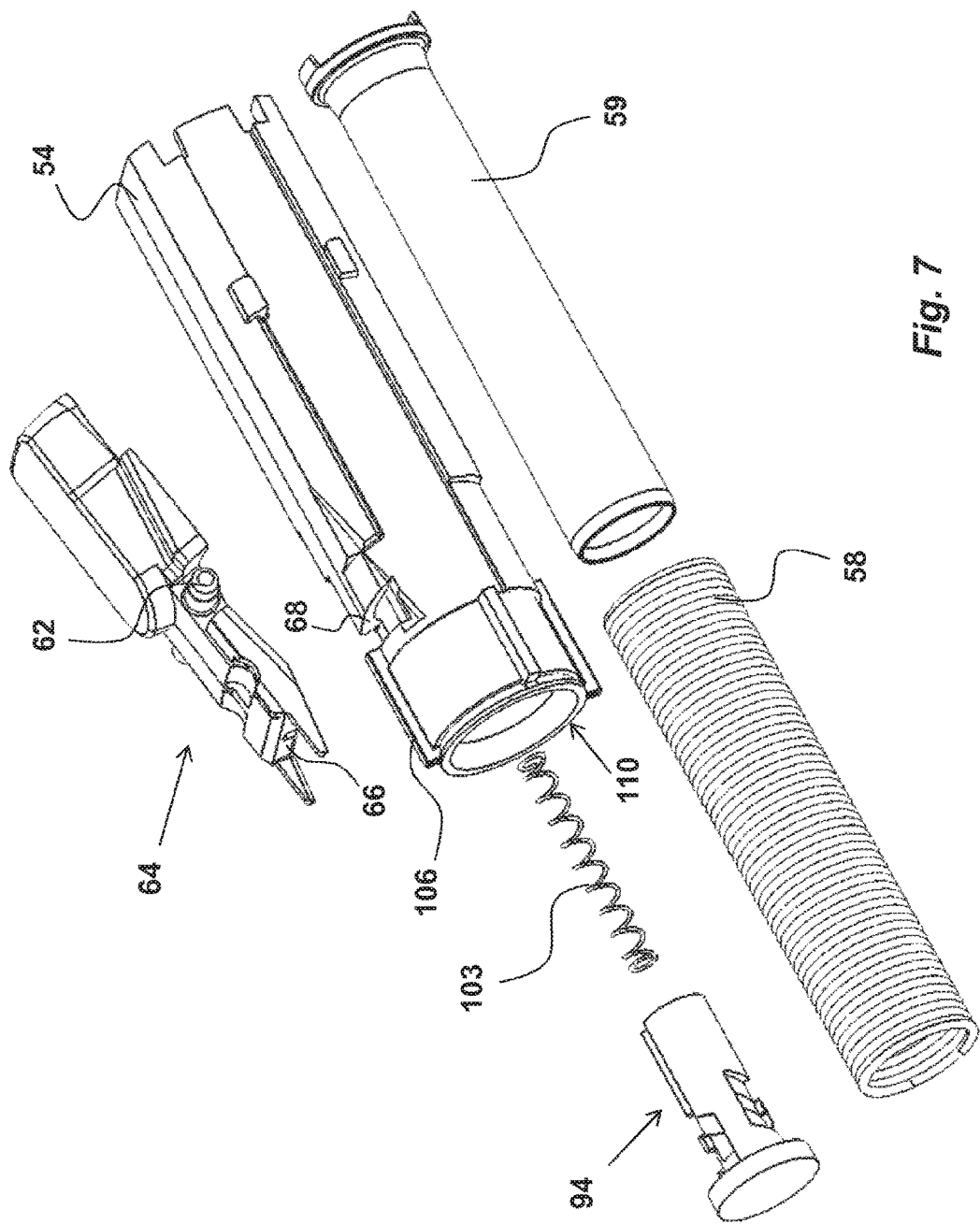

The device further comprises a drive mechanism, FIGS. 2 and 7. The drive mechanism is movable arranged in said housing between biased and released positions and vice versa when the drive mechanism is to be resettable. The drive mechanism comprises a plunger rod driver 54 arranged axially moveable within the main housing 10 as seen in FIG. 3. The proximal end of the plunger rod driver 54 is operably connected to a distal end of an elongated plunger rod 56, FIG. 2. The released position of the drive mechanism corresponds to a position of the plunger rod driver 54 where the plunger rod 56 and the stopper 22 have been pressed to the end of the stroke of the plunger rod 56, i.e. the medicament container 18 has been emptied, and the biased position of the drive mechanism corresponds to a position of the plunger rod driver 54 where the plunger rod 56 and the stopper 22 have not yet been moved, i.e. the medicament container 18 is full. The drive mechanism further comprises a drive element 58 for biasing the plunger rod driver 54 towards the proximal end of the device, here in the form of a helical coil spring, FIG. 7. The drive element 58 is supported by a tubular support element 59 that will prevent buckling of the drive element 58.

Figure 4:
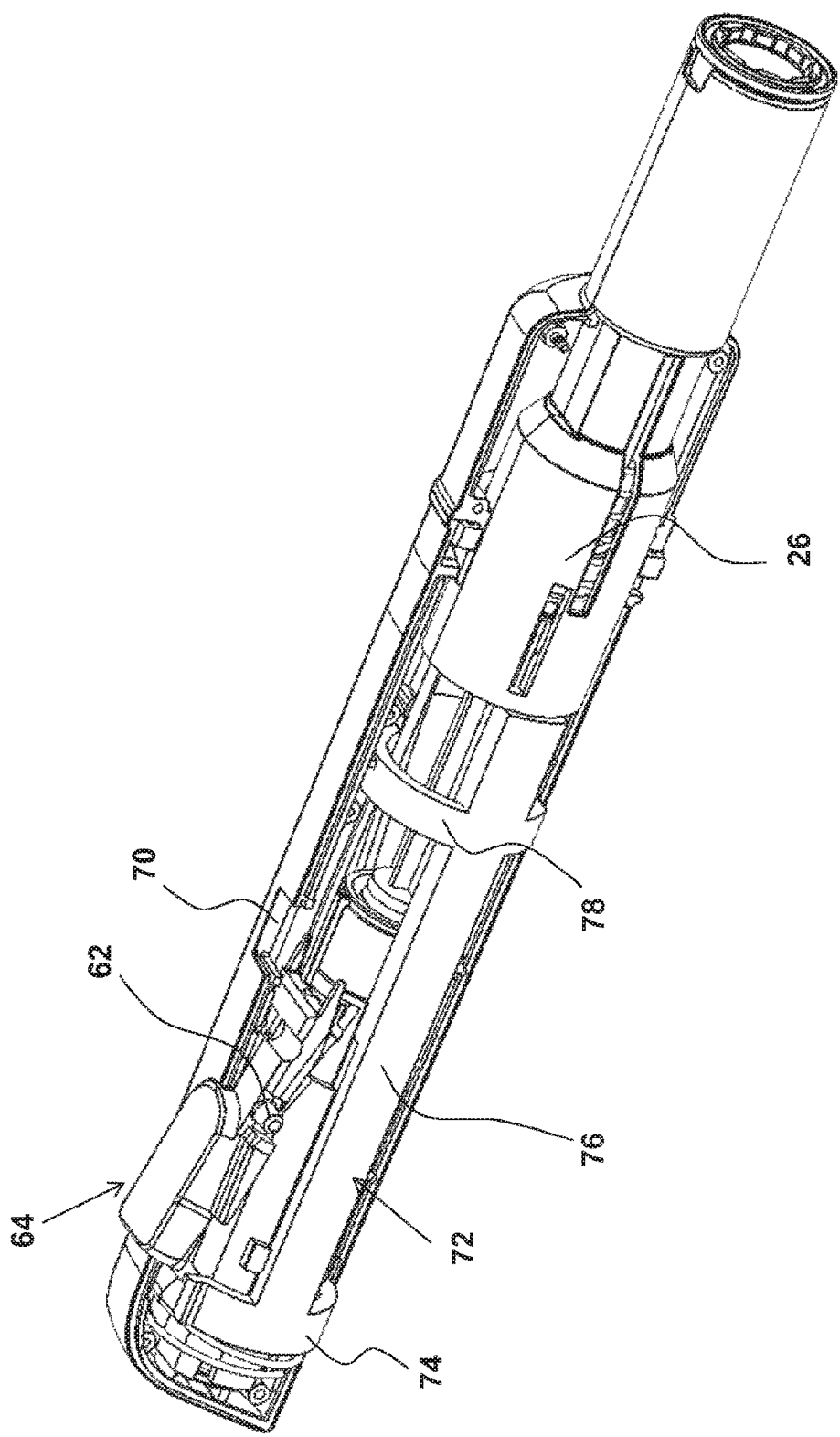
FIG. 4 is a perspective view of the embodiment of FIG. 1, with parts of a main housing removed for clarity.

The device also comprises a hold-release mechanism interactively connected to the drive mechanism for holding the drive mechanism in the biased position and releasing the drive mechanism from the biased position, FIGS. 2 and 7. The hold-release mechanism comprises an activation member 64 movable arranged in relation to the housing and having a locking element 66 configured to releasably lock the plunger rod driver 54 via a proximally directed ledge 68 to hold the plunger rod driver 54 with the drive element 58 in the biased position. The hold-release mechanism further comprises and a blocking member 72, FIGS. 4 and 8, movable arranged in relation to the activation member and configured to prevent the activation member to be actuated before the blocking member is actuated. The activation member 64 is pivotable around a pivoting axle 62, FIG. 7, between an extended position and a depressed position. The blocking member 72 comprises a generally ring-shaped blocking element 74 surrounding the plunger rod driver 54 and is in an initial position positioned distally of the hold-release mechanism such that a part of the blocking element 74 is under the distal end of the activation member 64 as seen in a radial direction, FIG. 4. In this position, the activation member 64 is prevented from pivoting around the pivoting axle, thus preventing the activation of the device. The ring-shaped blocking element 74 is arranged with two proximally and longitudinally extending arms 76, which arms 76 are inter-connected by a proximal ring-shaped second element 78. The arms 76 end in proximally directed end surfaces 80, FIG. 8. The proximally directed end surfaces 80 are arranged to be in contact with a distally directed end surface 82, FIG. 6, of the ,medicament delivery member shield 26, the function of which will be described below.

Adjacent, or at least near the hold-release mechanism, a status window 70 is arranged through which symbols provided on the plunger rod driver 54 are visible to indicate the status of the medicament delivery device. The status window 70 is preferably made of a transparent, or at least translucent, plastic material.

Figure 9:
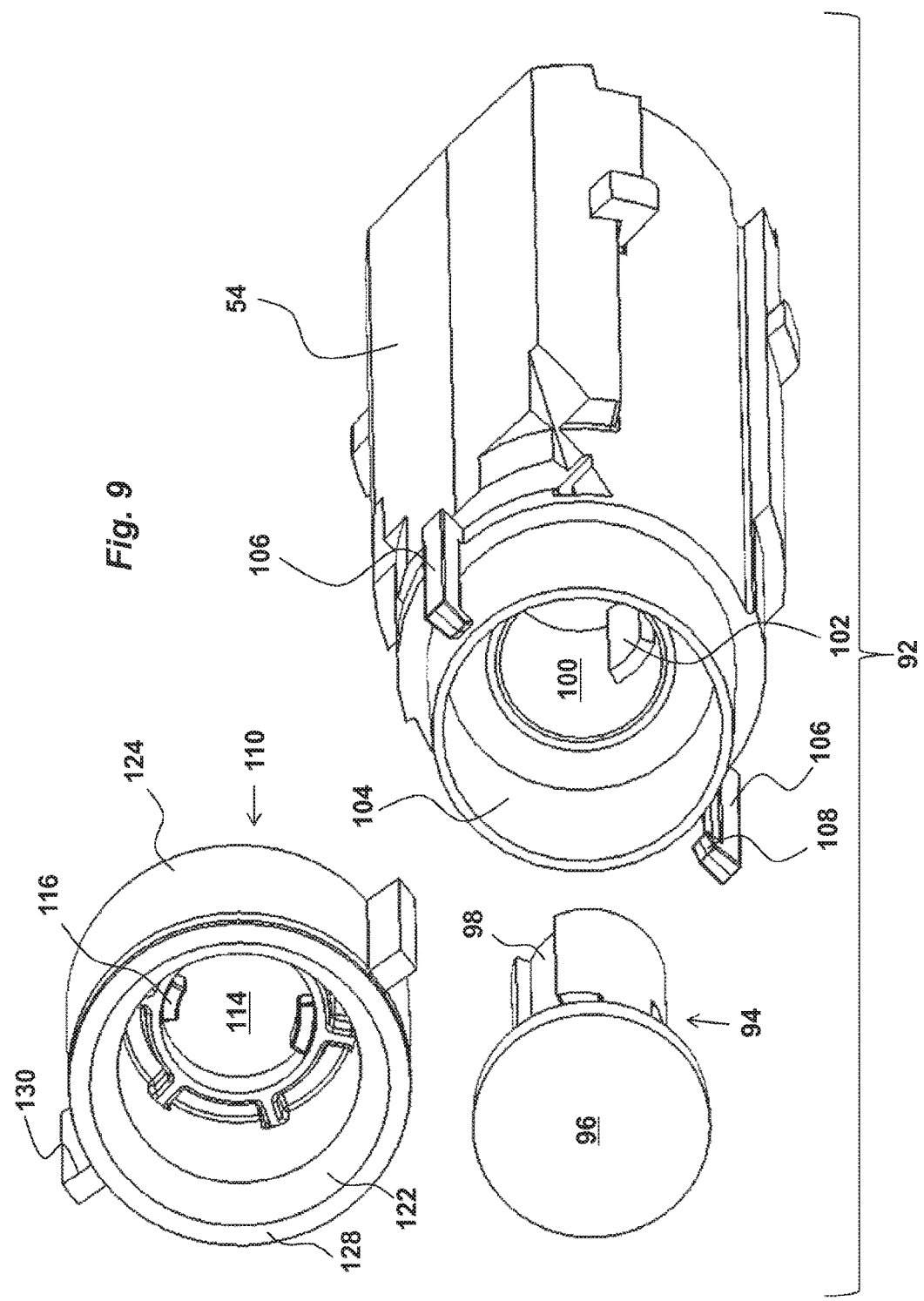
Figure 10:
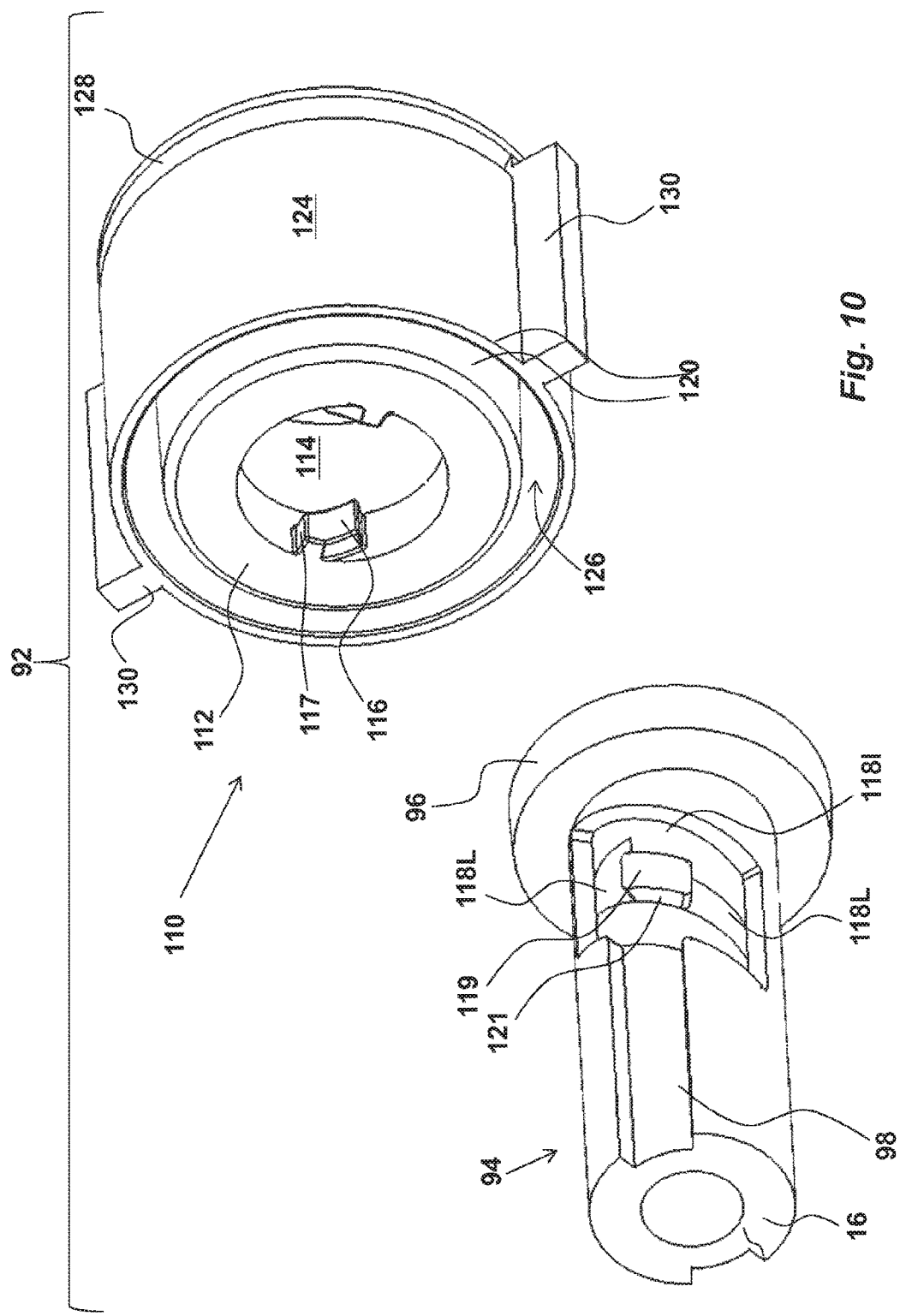

The device further comprises a delayable signal generating mechanism 92, FIGS. 9 and 10, interactively connected to the drive mechanism and which is releasably connected to the hold-release mechanism such that when the plunger rod nears or reaches the end of its operating stroke, the delayable signal generating mechanism is released from the hold-release mechanism whereby the delayable signal generating mechanism is enabled to interact with the drive mechanism for generating an audible and/or tactile and/or visual signal indicating that a medicament has been completely delivered.

The delayable signal generating mechanism 92 comprises a signal generating element 94 and a delay element 110 configured to be releasably connected to each other as be explained in detail below. The signal generating element 94 has the shape of an elongated tubular body, provided with a circular end plate 96, with a proximally directed end surface, which is intended to be in contact with a distally directed end surface of the plunger rod 56. Thus, the plunger rod driver 54 is operably arranged to the plunger rod 56 via said signal generating element 94.

The signal generating element 94 is connected to the plunger rod driver 54 by a connection configured to restrict a rotational displacement but to allow an axial displacement between said signal generating element and said plunger rod driver, as will be explained below. Further, the delay element 110 is connected to the plunger rod driver 54 by a connection configured to restrict an axial displacement but to allow a rotational displacement between said delay element and said plunger rod driver 54, as will be explained below. Also, the blocking member 72 and the delay element 110 are releasably connected to each other by first guide and hold elements configured to hold the delay element in a non-movable state in relation to the plunger rod driver 54 when the plunger rod driver 54 is locked by the locking element 66 of the activation member 64 and to guide the displacement of the delay element 110 towards the proximal end of the device when the plunger driver is released by the activation member 64 such that the displacement of the delay element 110 is an axial displacement in relation to the blocking member 72. Moreover, the delay element 110 and the signal generating element 94 are releasably connected to each other by second guide and hold elements configured:—to hold the signal generating element 94 and the delay element 110 in a non-displaceable state in relation to each other when the delay element 110 together with the plunger rod driver 54 are axially displaced in relation to the blocking member 72 towards the proximal end of the device;—to promote a rotational displacement of the delay element 110 in relation to the signal generating element 94 when the delay element 110 is released from the blocking member 72; and—to guide an axial displacement of the signal generating element 94 in relation to the delay element 110 towards the distal end of the device when the signal generating element 94 is released from the delay element 110 whereby the delay element 110 together with the plunger rod driver 54 continue to be axially displaced in relation to the blocking member 72 towards the proximal end of the device such that a distal end surface of the signal generating element 94 hits a proximal end surface of the plunger rod driver 54 whereby the audible and/or tactile and/or visual signal indication that a medicament has been completely delivered is generated. The rotational displacement of the delay element 110 in relation to the signal generating element 94 is rotationally damped by a viscous media arranged between the the delay element 110 and the signal generating element 94.

Figure 13:
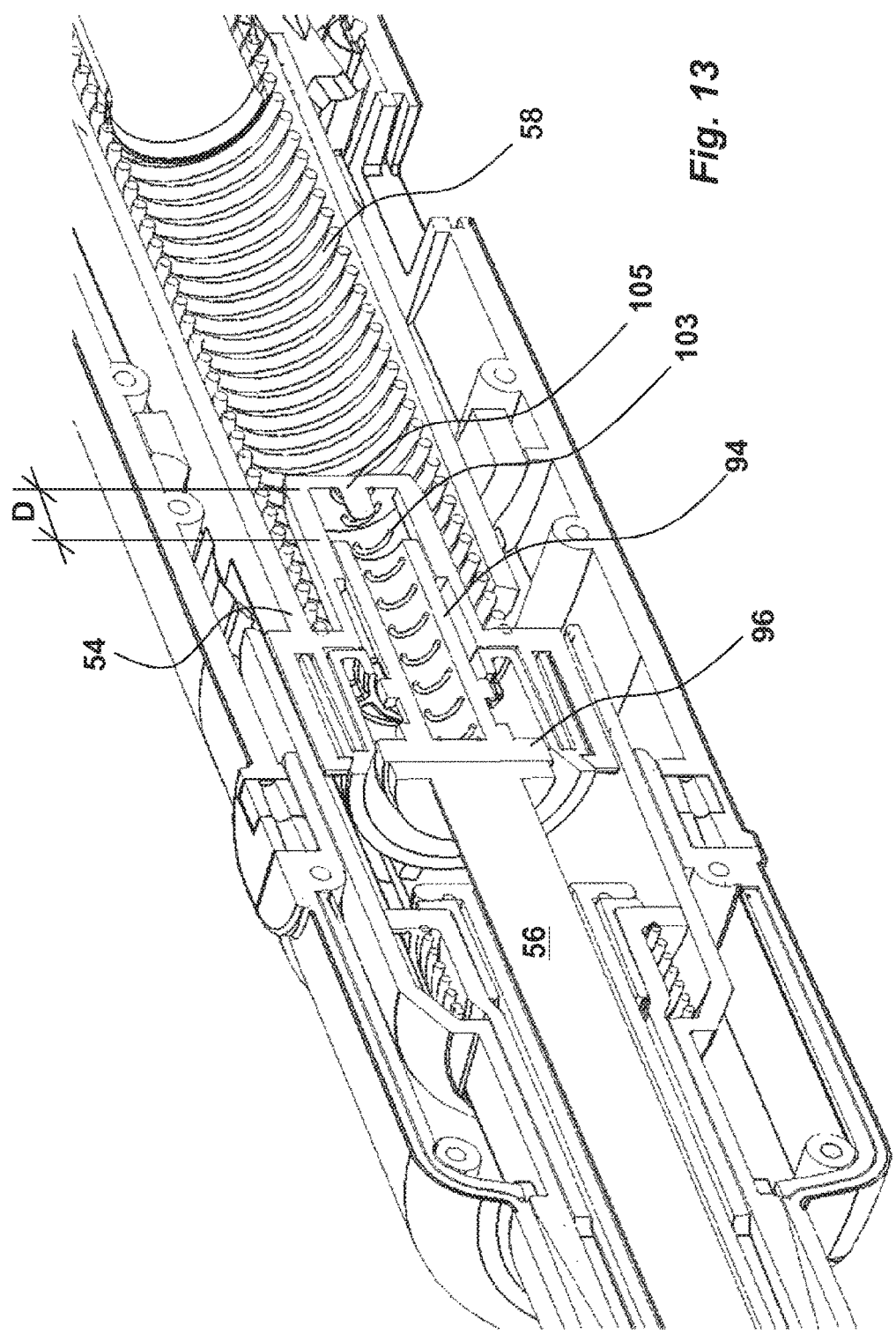

A signal generating element spring 103, FIGS. 7 and 13, is arranged between a proximally directed end wall 105 at the proximal end of the plunger rod driver 54 and a distally directed surface of the circular end plate 96 inside the tubular body of the signal generating element 94. The signal generating element spring 103 is configured to be compressed during medicament delivery.

Figure 8:
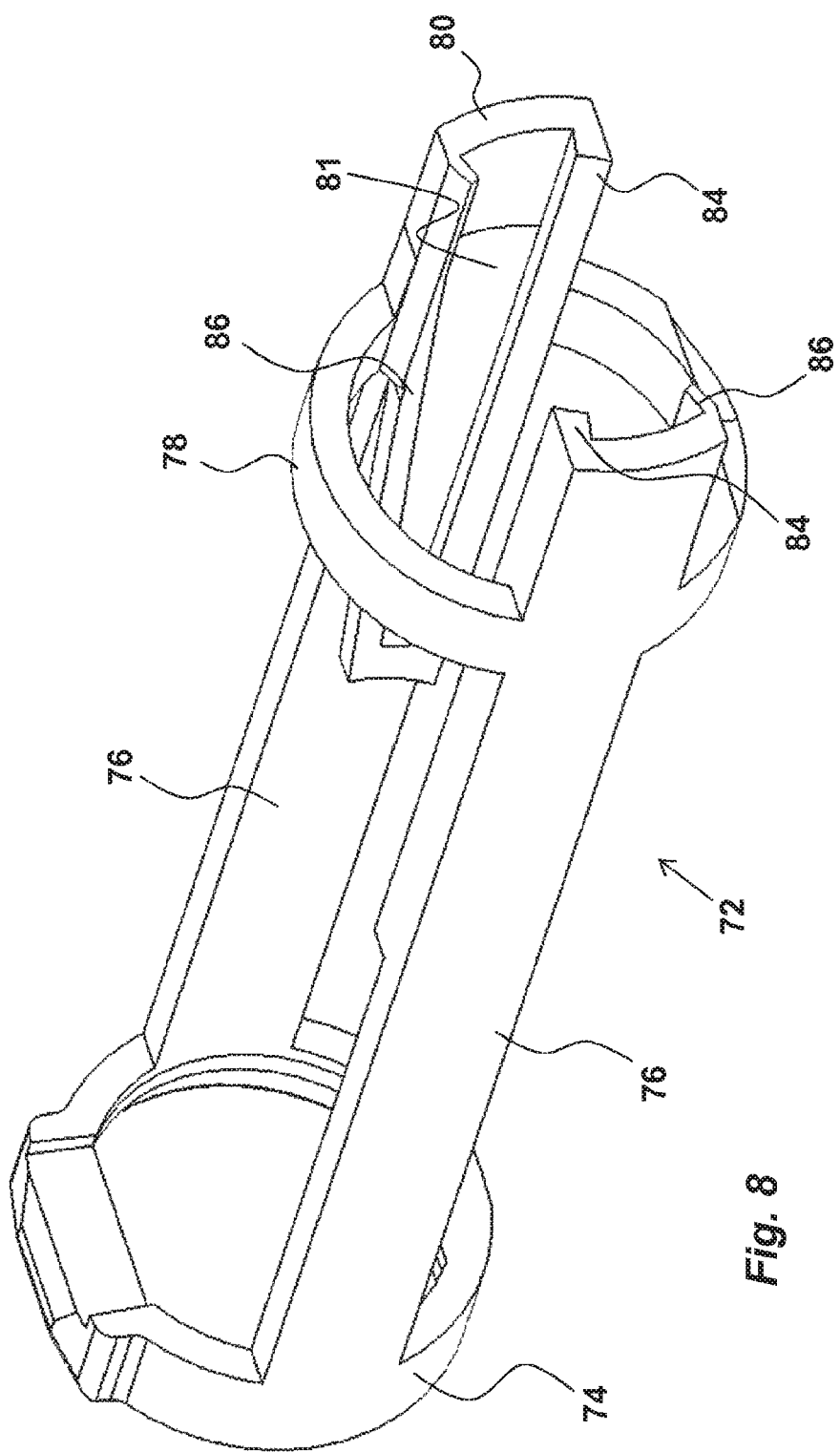

The first guide and hold elements comprise guide tracks 81, FIG. 8, arranged on the inner surfaces of longitudinally extending arms 76 of the blocking member 72 and radially extending ledges 130 arranged on the outer surface of the delay element 110. The guide tracks 81 are formed by elongated ledges 84, 86, FIG. 8. One of the ledges 84 runs parallel with the longitudinal axis of the device while the other ledge 86 is somewhat inclined as seen in FIG. 8. As seen in the figure, the lower ledge 84 is parallel while the upper ledge 86 is inclined on one arm. On the opposite arm the upper ledge 84 is parallel while the lower ledge 86 is inclined. The function of the ledges will be described in detail below.

The second guide and hold elements comprise guide tracks 118 and a central radially extending protrusion 119 arranged on the outer circumferential surface of said signal generating element 94 and a radial inwardly extending protrusion 116 arranged on the inner circumferential surface of said delay member 110, FIGS. 9 and 10.

Further, the outer circumferential surface of the signal generating element 94 is arranged with longitudinally extending guide tracks 98, FIGS. 9 and 10. The signal generating element 94 is arranged to fit into a central passage 100 at the proximal end of the plunger rod driver 54, FIG. 10. The guide tracks 98 on the signal generating element 94 are intended to interact with longitudinally extending ledges 102 in the passage 100 of the plunger rod driver 54. As mentioned above, this connection is configured to restrict a rotational displacement but to allow an axial displacement between said signal generating element 94 and said plunger rod driver 54.

Further, the plunger rod driver 54 is arranged with a tubular body 104, FIG. 9, arranged coaxial with the passage 100 and extending in the proximal direction. Radially outside the tubular body 104 two arms 106 are extending in the proximal direction, where the arms 106 are positioned on opposite sides of the tubular body 104. Each arm 106 is arranged with a generally radially inwardly directed ledge 108. The tubular body 104 and the arms 106 are intended to cooperate with a delay element 110. The delay element 110 comprises a hub 112 provided with a central passage 114. The inner surface of the passage 114 is arranged with the protrusions 116 positioned opposite each other. The protrusions 116 are arranged with inclined side surfaces 117. The protrusions 116 are arranged to fit into the guide tracks 118 on the outer circumferential surface of the signal generating element 94, which guide tracks 118 comprise both longitudinally extending sections 118L as well as inclined sections 118I as seen in FIG. 10. The design of the groove sections 118 forms the central protrusion 119 as seen in FIG. 10 with inclined distally directed side surface 121.

The hub 112 is further provided with a generally tubular first body 120 extending in the longitudinal direction. At the proximal end of the first body 120 an annular wall 122, FIG. 9, is provided. A second tubular body 124 is attached to the annular wall 122 such that an annular compartment 126, FIG. 10, is provided between the first and the second tubular bodies 120, 124. The delay element 110 and the plunger rod driver 54 are thus designed such that the tubular body 104 fits into the compartment 126 when the delay element 110 is inter-connected with the plunger rod driver 54, as seen in FIG. 7, such that gaps are formed between the first tubular body of the delay element 110 and the tubular body 104 of the plunger rod driver 54 as well as between the tubular body 104 of the plunger rod driver 54 and the second tubular body 124 of the delay element 110. The gaps are filled with a viscous fluid capable of creating a damping shear force when the delay element 110 is moved in relation to the plunger rod driver 54, as will be described.

The delay element 110 is held in place by the ledges 108 of the arms 106 of the plunger rod driver 54 fitting into an annular ledge 128 on the outer surface of the delay element 110. Thus, as mentioned above, the plunger rod driver 54 and the delay element 110 are connected by a connection configured to restrict an axial displacement but to allow a rotational displacement between said delay element and said plunger rod driver.

The medicament delivery member shield 26 is interactively connected to the delay element 110 by a connection configured to allow a rotation the delay element 110 in relation to the signal generating element 94 after the medicament has been delivered and the housing parts are rotated in relation to each other such that when the housing parts are separated the signal generating element 94 is axially displaced towards the proximal end of the device by the force of the signal generating element spring 103. Thus, the elongated ledges 31 on the inner surface of the medicament delivery member shield 26 interact with the radially extending ledges 130 of the delay element 110.

The device is intended to function as follows. When the device is delivered to the user, the medicament delivery member shield 26 is in an extended, proximal position where the medicament delivery member 20 is shielded, FIG. 8. There is thus no risk for unintentional needle sticks. The plunger rod 56 is in a distal position where the plunger rod driver 54 is locked in the biased position with the drive element 58 compressed as seen in FIG. 3.

Figure 11:
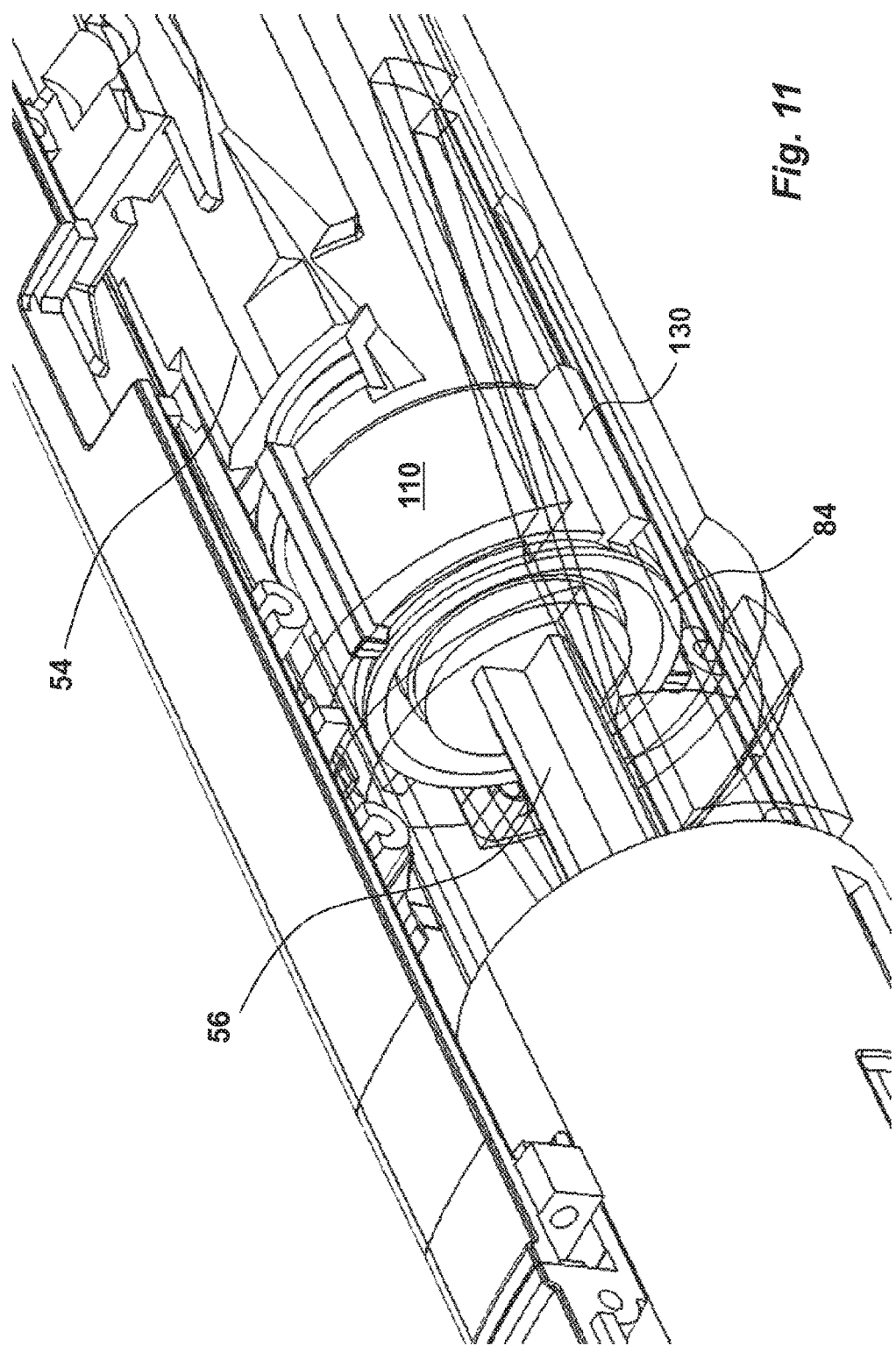

The user then presses a proximal end of the medicament delivery member shield 26 against a dose delivery site, whereby the medicament delivery member shield 26 is moved towards the distal direction inside the housing of the device, FIG. 11. Upon pressing the device against the dose delivery site, the medicament delivery member shield 26 also comes into contact with the proximally directed end surfaces 80 of the arms 76 of the blocking member 72. Thus the ring-shaped blocking element 74 of the blocking member 72 is moved out of blocking position, allowing the hold-release mechanism to be activated. The next step is then for the user to activate the dose delivery sequence.

According to the embodiment shown, the user depresses the activation member 64 of the hold-release mechanism, whereby the drive element 58 is released in that the locking element 66 is moved out of contact with the plunger rod driver 54. The plunger rod driver 54 and the drive element 58 then acts to force the plunger rod 56 in the proximal direction acting on the stopper 22 inside the medicament container 18. Since the medicament is incompressible and the passage through the medicament delivery member 20 is narrow, the medicament container holder 24 with the medicament container 18 will be moved towards the proximal direction, against the rather weak force of the medicament delivery member return force element 44.

The movement of the medicament container 18 will now cause a penetration of the medicament delivery member 20 into the skin of the user. The force of the drive element 58 is far more powerful than that of the medicament delivery member return force element 44, which therefore is compressed when the drive mechanism is released. The penetration movement is stopped when the circumferential ledge (not shown) of the distal end of the medicament container holder is adjacent a distally directed stop ledge 46 of the medicament delivery member shield 26 with the fully compressed medicament delivery member return force element 44 between the ledges.

The force of the drive element 58 now forces the plunger rod 56 in the proximal direction in relation to the medicament container 18, moving the stopper 22 in the proximal direction, whereby a dose of medicament is delivered into the body of the user. When the plunger rod 56 is moving towards the proximal direction, so is the signal generating element 94. The signal generating element 94 is rotationally locked to the plunger rod driver 54 by the ledges 102 of the plunger rod driver 54 positioned in the guide tracks 98 of the signal generating element 94. The signal generating element 94 is urged in the distal direction due to that it is pushed towards the stopper 22 but is held stationary in relation to the plunger rod driver 54 because the delay element 110 is positioned such in relation to the signal generating element 94 that the protrusions 116 of the delay element 110 are abutting the distally directed side surface 121 of the central protrusion 119 as seen in FIG. 11.

The inclination of the side surface 121 of the central protrusion 119 as well as the inclination of the side surfaces 117 of the protrusions 116 will attempt to rotate the delay element 110 but this rotation is prevented by the radially directed ledges 130 that are arranged in the guide tracks 81, as seen in FIG. 11. When the plunger rod driver 54, the signal generating element 94, the plunger rod 56 and the stopper 22 have reached a position close to the proximal end position of the stopper 22, the guide tracks 81 terminate.

Due to the inclined distally directed side surface 121 as well as the inclined surfaces 117 of the protrusions 116 the force from the drive element 58 will urge the delay element 110 to turn in relation to the plunger rod driver 54 and also in relation to the signal generating element 94 since it is rotationally locked with the plunger rod driver 54. However, the turning of the delay member 110 is slow due to the damping grease acting between the components, which acts between the moving surfaces in the gaps. During this time, the stopper 22 reaches its proximal end position and the dose delivery sequence has ended.

Figure 14:
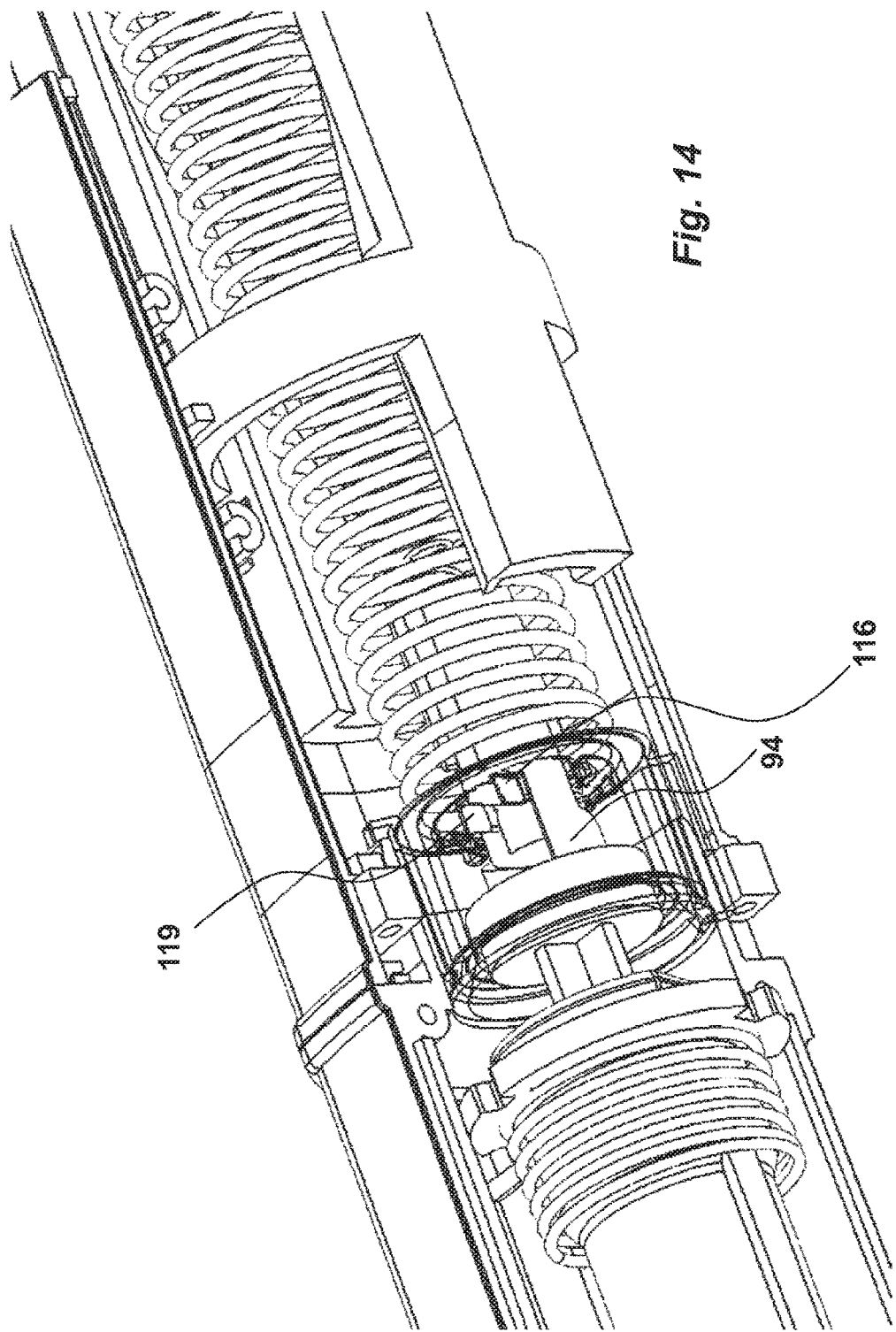
Figure 15:
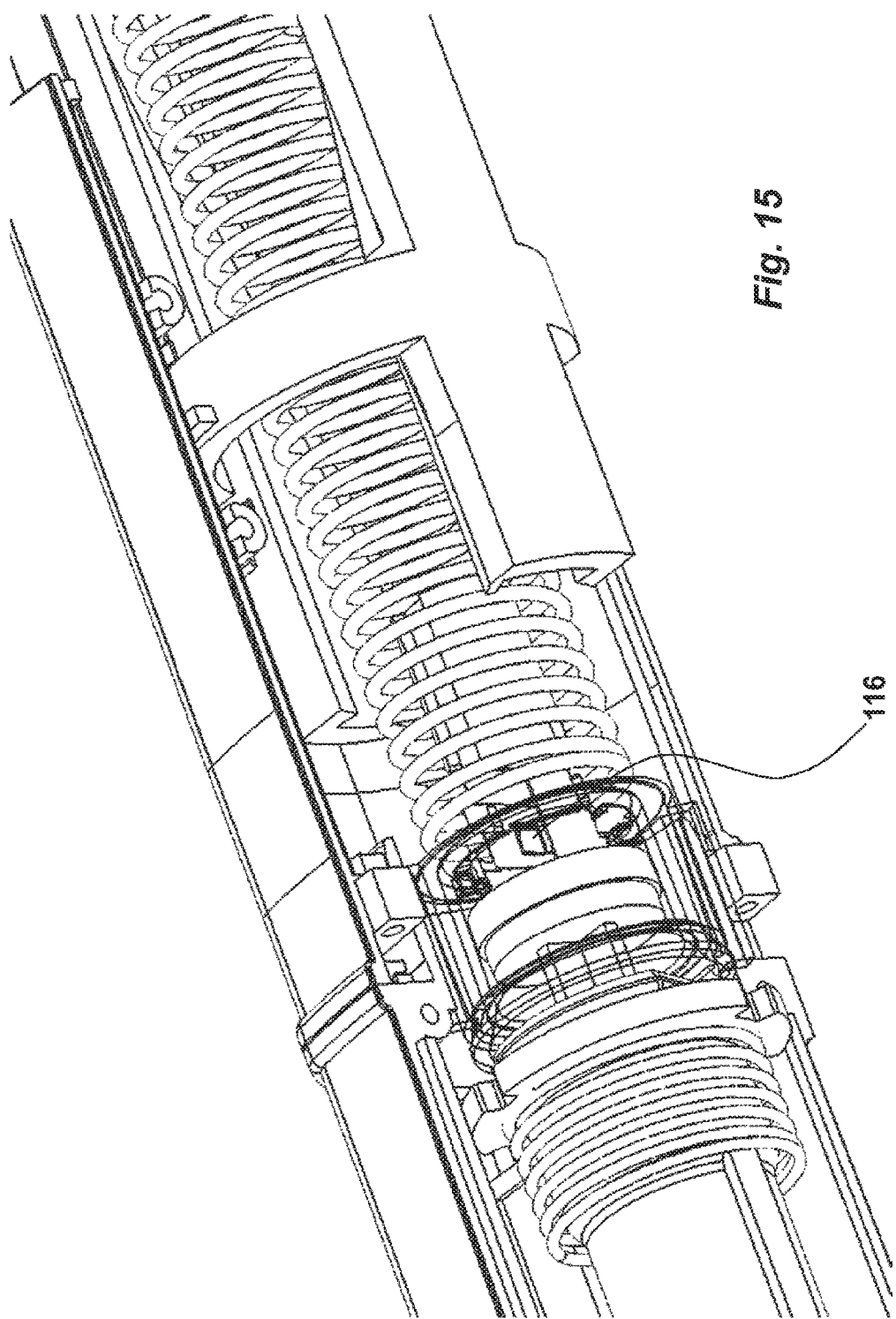
Figure 16:
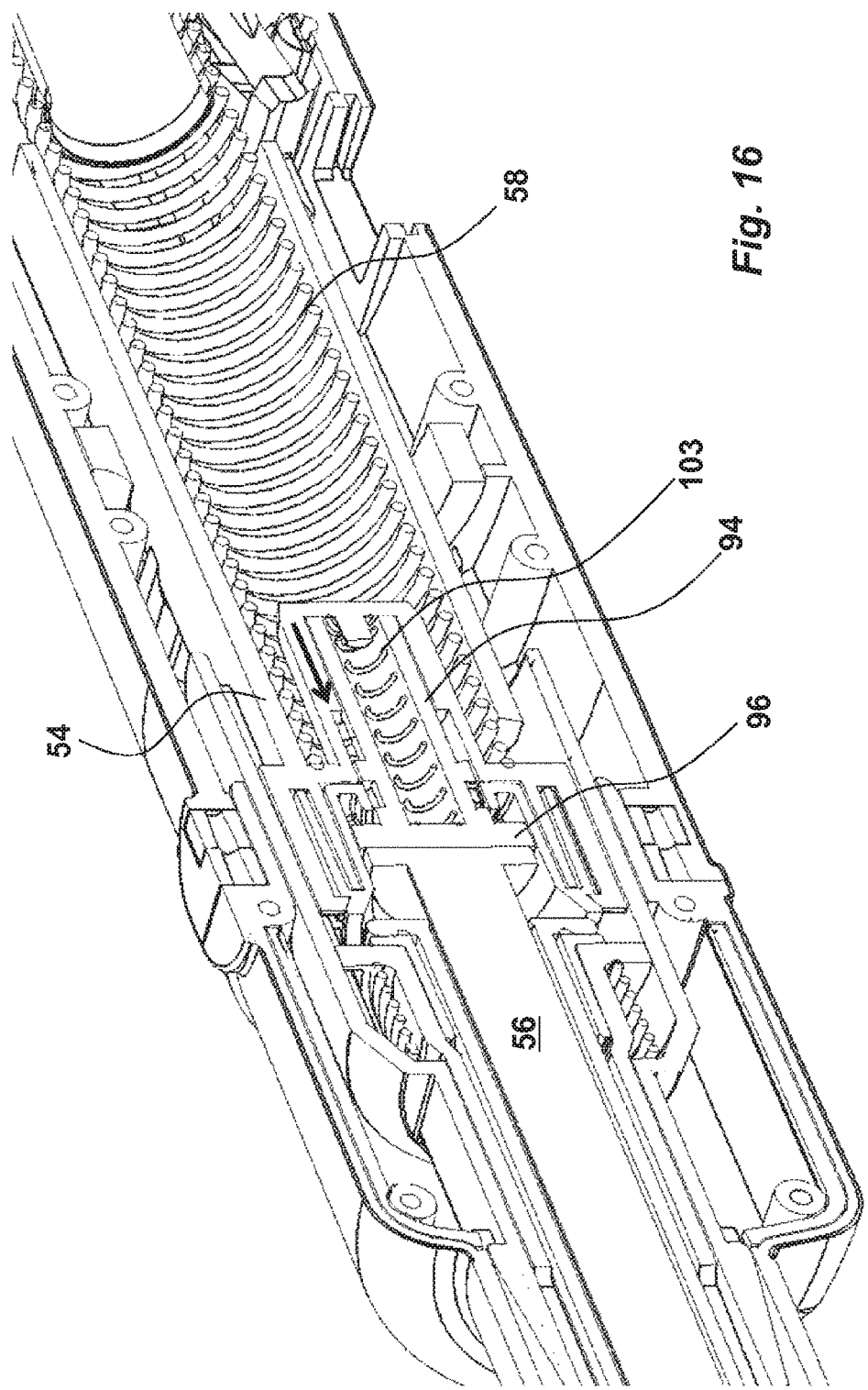

The turning of the delay element 110 continues until its protrusions 116 move out of contact with the central protrusion 119 of the signal generating element 94, FIG. 14. The connection between the plunger rod driver 54 and the signal generating element 94 in the longitudinal direction is now lost and the plunger rod driver 54 is free to move in the proximal direction by the force of the drive element 58, and due to the force the plunger rod driver 54 will move with a certain speed a predetermined distance D until it hits the distal end surface of the signal generating element 94 with the end surface 105. The contact will cause an audible signal as well as a tactile signal. The signals will inform the user that it is safe to remove the device from the dose delivery site.

When removing the device, since the force on the medicament delivery member shield 26 now is removed at its proximal end, the medicament delivery member return force element 44 will force the medicament delivery member shield 26 in the proximal direction, whereby the medicament delivery member 20 is again shielded by the medicament delivery member shield 26. In its extended position, the medicament delivery member shield 26 is locked by a medicament delivery member shield locking mechanism (not shown).

Figure 17:
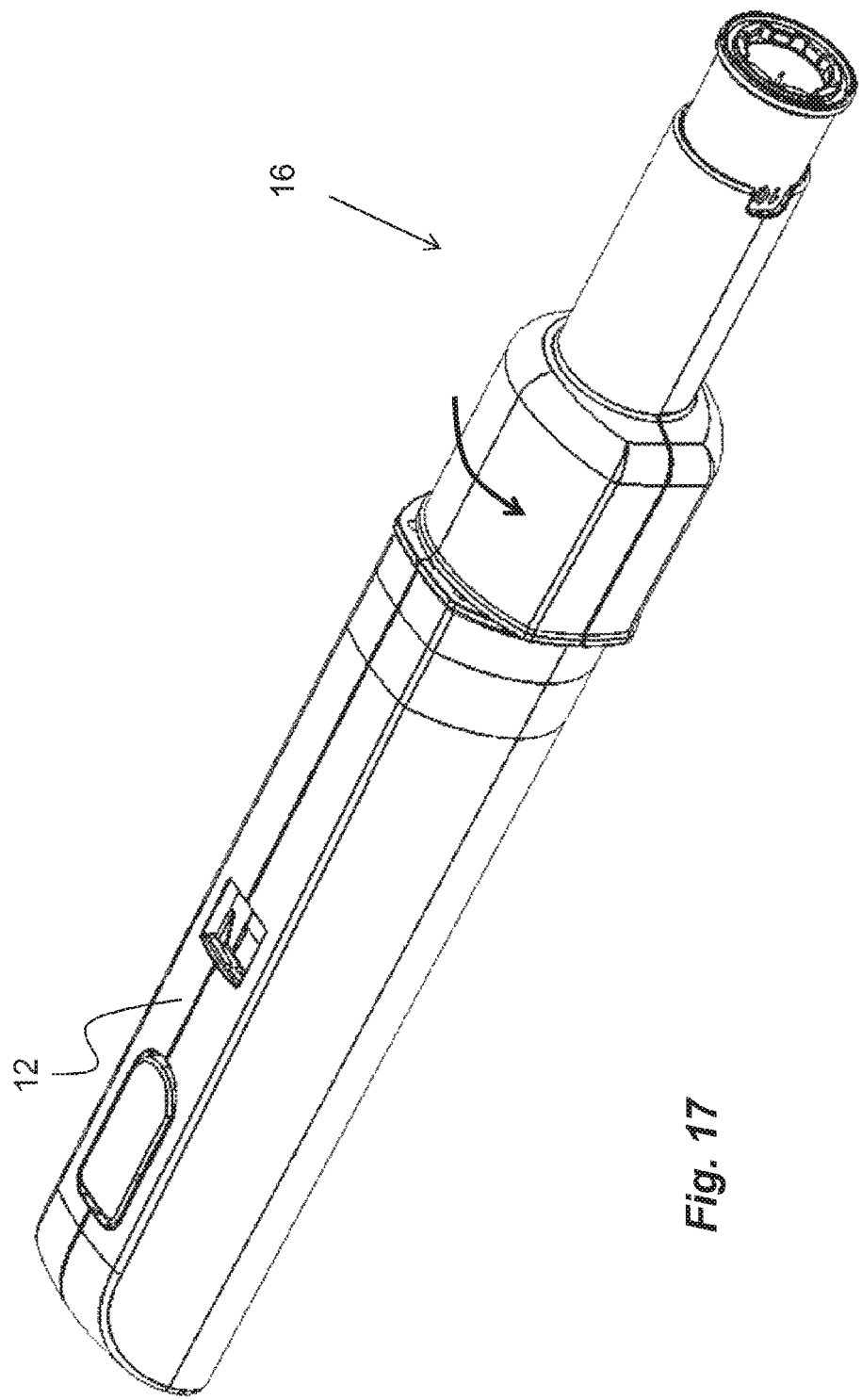
Figure 18:
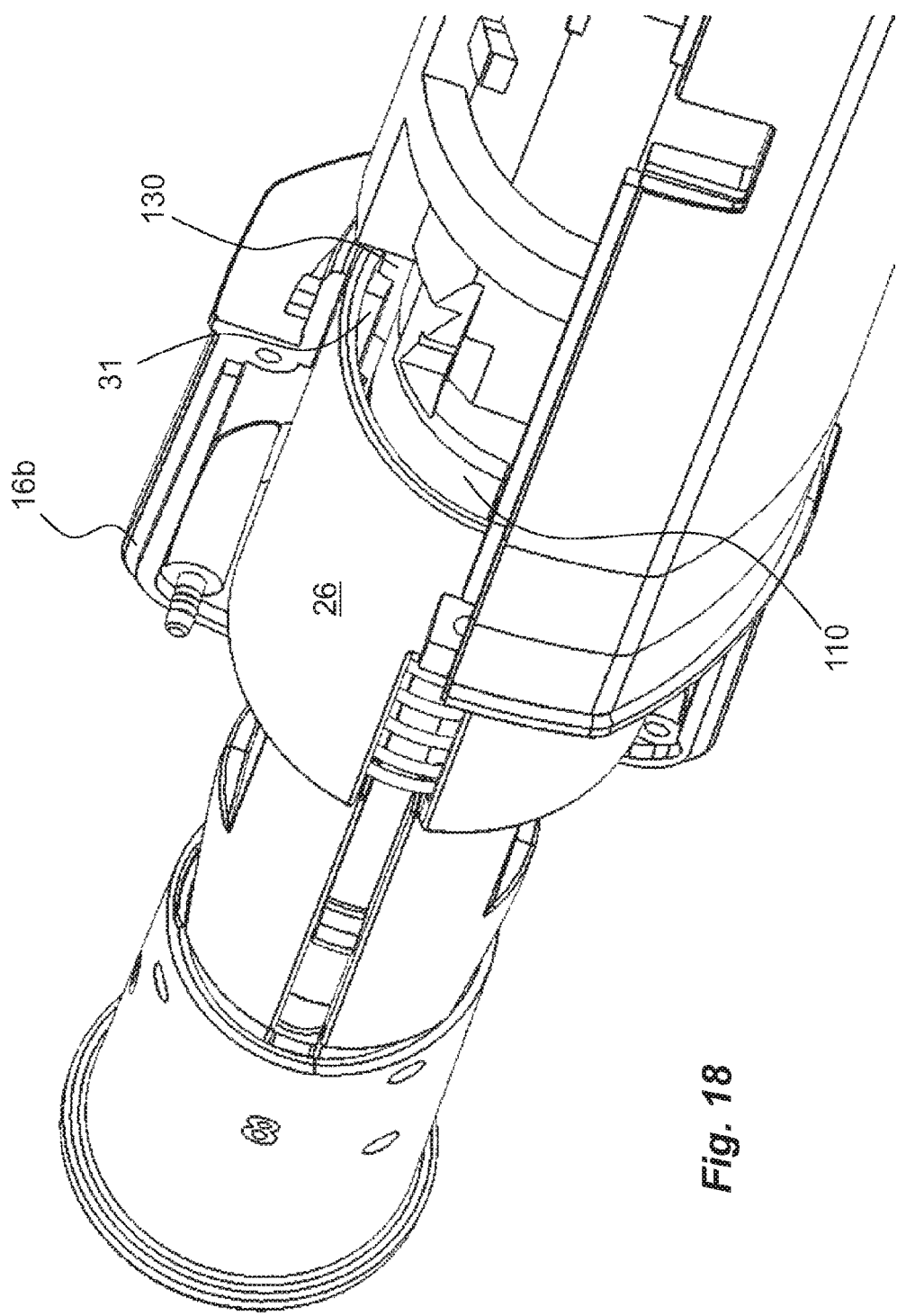
Figure 19:
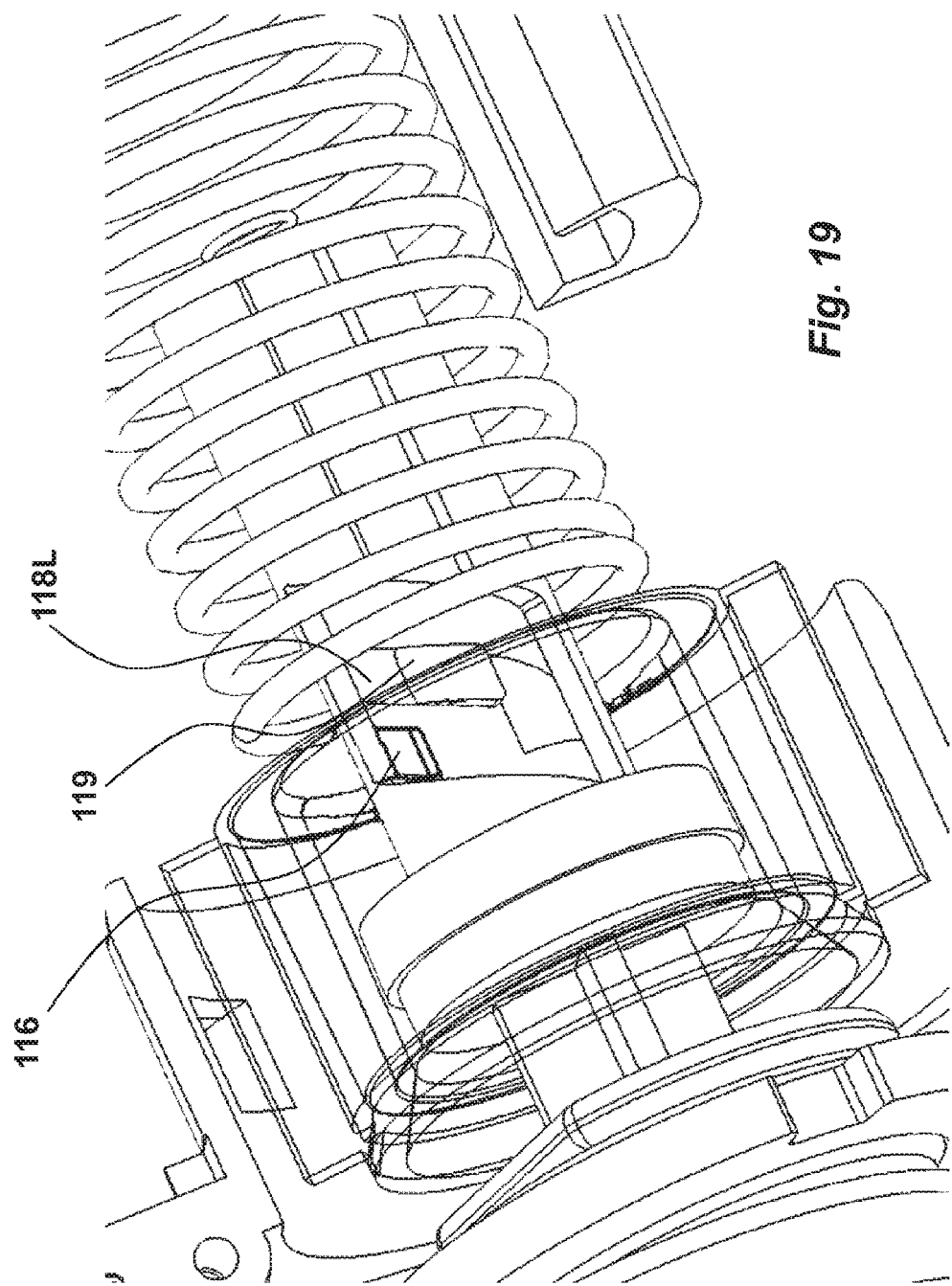
Figure 20:
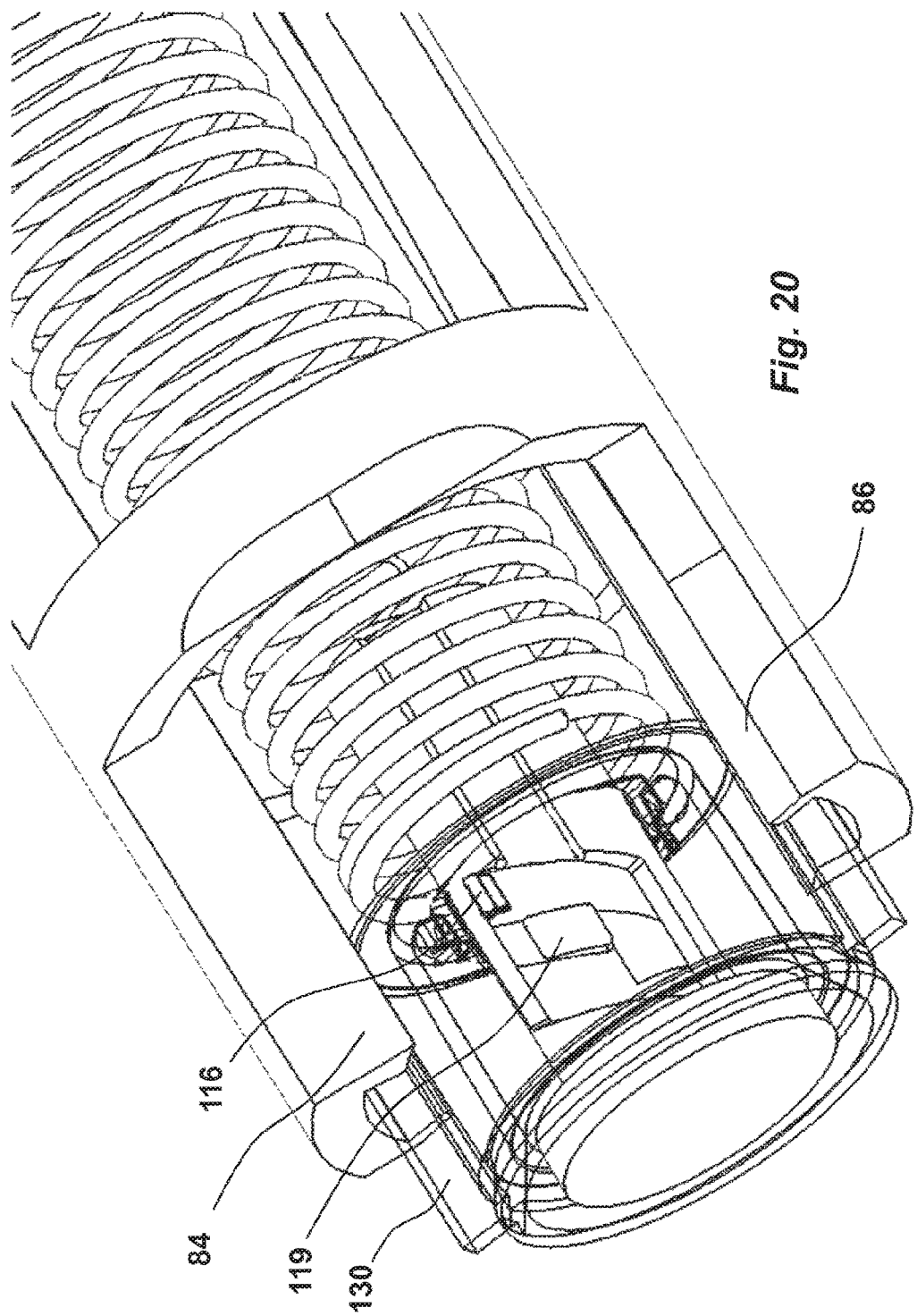

When the device is to be used again, the proximal housing part 16 is removed from the main housing part 10. This may be done by turning the housing parts in relation to each other, if for instance a bayonet connection is used, as seen in FIG. 17. This turning causes the delay element 110 to be turned due to the elongated ledge 31 on the inner surface of the medicament delivery member shield 26 acting on one of the radially extending ledges 130 of the delay element 110 as seen in FIG. 18. The protrusions 116 of the delay element 110 will then be in the position in the guide tracks 118L of the signal generating element 94 as seen in FIG. 19. When the proximal housing part then is removed from the distal housing part, the signal generating element 94 will be pushed in the proximal direction by the signal generating element spring 103 so that the protrusions 116 of the delay element 110 will be positioned in the guide tracks 118I of the signal generating element 94 as shown in FIG. 20.

Figure 12:
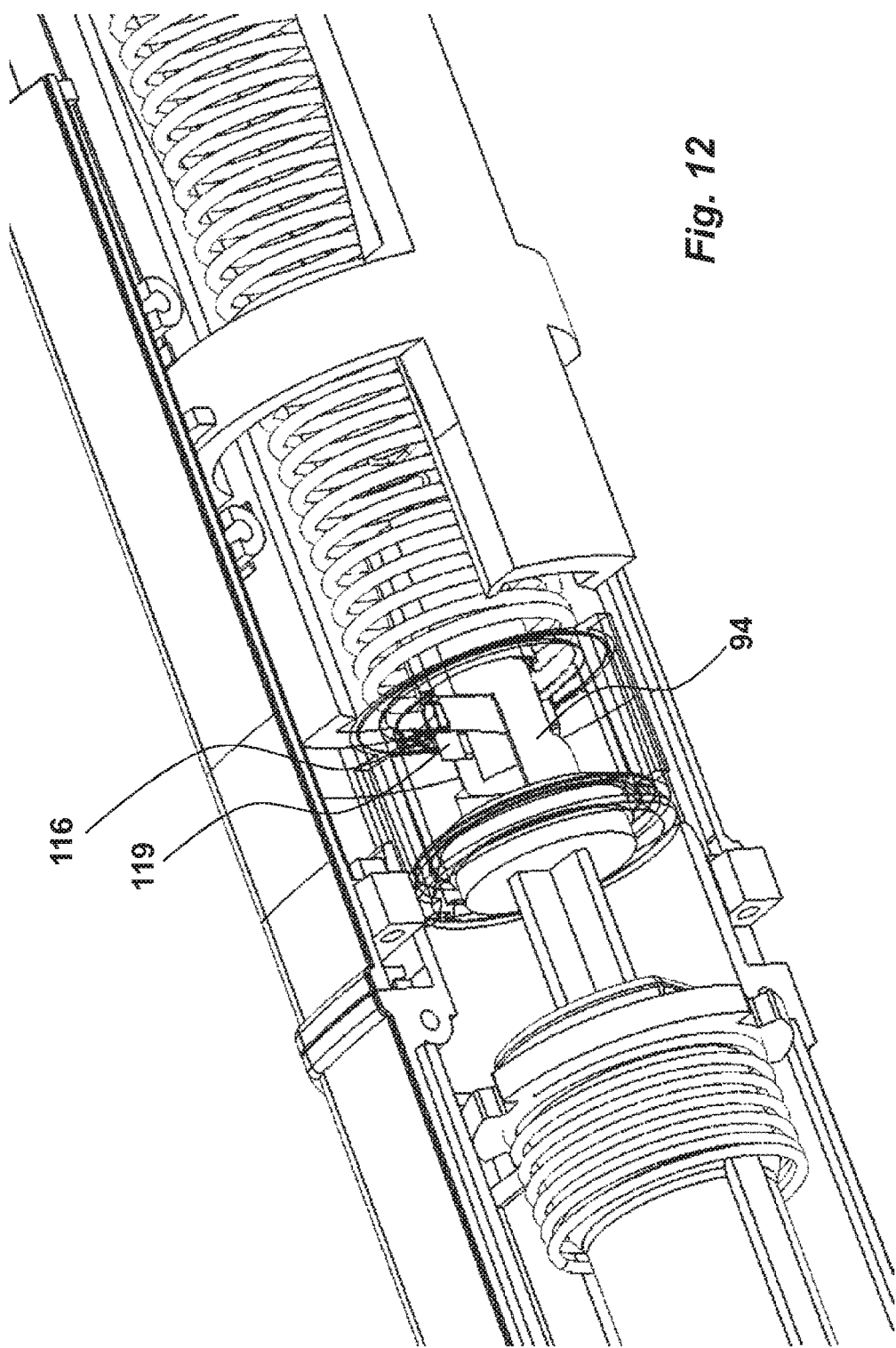

In order to reset the device the plunger rod driver 54 has to be moved back to its initial position. This may be done by pushing on the plunger rod driver 54 in the distal direction with a suitable tool. This will cause the drive element 58 to be again tensioned until the locking element 66 grips and holds the plunger rod driver 54. Further, the movement in the distal direction will cause the radial ledges 130 of the delay element 110 to come in contact with the inclined ledges 86 of the arms 76, causing a slight turning of the delay element 110 such that the protrusions 116 will be moved back to the initial position distal of the central protrusion 119 as shown in FIG. 12. Thus the device is again reset and loaded for subsequent use. The proximal housing part 16 will now be loaded with a new medicament container and the proximal housing part 16 will be connected with the main housing 10 by turning and locking the housing parts in relation to each other.

It is to be understood that the embodiment described above and shown in the drawings is to be regarded only as a non-limiting example of the invention and that it may be modified in many ways within the scope of the patent claims.

The invention claimed is:

1. A medicament delivery device extending along a longitudinal axis and comprising:
   a housing having a distal and a proximal end, said housing being adapted to receive a medicament container;
   a drive mechanism comprising a plunger rod driver movable in said housing between biased and released positions and arranged to act on a plunger rod, which plunger rod in turn is arranged to act on the medicament container;
   a hold-release mechanism interactively connected to the drive mechanism for holding the drive mechanism in the biased position and releasing the drive mechanism from the biased position; and
   a delayable signal generating mechanism comprising a signal generating element interactively connected to the drive mechanism, where
   the delayable signal generating mechanism is releasably connected to the hold-release mechanism such that when the plunger rod nears or reaches the end of its operating stroke, the delayable signal generating mechanism is released from the hold-release mechanism whereby the delayable signal generating mechanism is enabled to interact with the drive mechanism for generating an audible and/or tactile and/or visual signal indicating that a medicament has been completely delivered,
   wherein said plunger rod driver is operably arranged to said plunger rod via said signal generating element.

2. The medicament delivery device according to claim 1, wherein said delayable signal generating mechanism comprises a delay element configured to be releasably connected to each other.

3. The medicament delivery device according to claim 2, wherein said drive mechanism comprises a drive element for biasing the plunger rod driver towards the proximal end of the device.

4. The medicament delivery device according to claim 3, wherein the signal generating element is connected to the plunger rod driver by a connection configured to restrict a rotational displacement but to allow an axial displacement between said signal generating element and said plunger rod driver.

5. The medicament delivery device according to claim 3, wherein said delay element is connected to said plunger rod driver by a connection configured to restrict an axial displacement but to allow a rotational displacement between said delay element and said plunger rod driver.

6. The medicament delivery device according to claim 5, wherein the connection between the delay element and the plunger driver is rotationally damped for regulating the rotational speed of said delay element.

7. The medicament delivery device according to claim 3, wherein said hold-release mechanism comprises an activation member movable arranged in relation to the housing and having a locking element configured to releasably lock the plunger rod driver, and a blocking member movable arranged in relation to the activation member and configured to prevent the activation member to be actuated before the blocking member is actuated.

8. The medicament delivery device according to claim 7, wherein said blocking member and said delay element are releasably connected to each other by first guide and hold elements configured to hold the delay element in a non-movable state in relation to the plunger driver when the plunger driver is locked by the locking element of the activation member and to guide the displacement of the delay element towards the proximal end of the device when the plunger driver is released by the activation member such that the displacement of the delay element is an axial displacement in relation to the blocking member.

9. A medicament delivery device according to claim 8, wherein said delay element and said signal generating element are releasably connected to each other by second guide and hold elements configured:
to hold the signal generating element and said delay element in a non-displaceable state in relation to each other when the delay element together with the plunger driver are axially displaced in relation to the blocking member towards the proximal end of the device;
to promote a rotational displacement of the delay element in relation to the signal generating element when the delay element is released from the blocking member; and
to guide an axial displacement of the signal generating element in relation to the delay element towards the distal end of the device when the signal generating element is released from the delay element whereby the delay element together with the plunger driver continue to be axially displaced in relation to the blocking member towards the proximal end of the device such that a distal end surface of the signal generating element hits a proximal end surface of the plunger driver whereby the audible and/or tactile and/or visual signal indication that a medicament has been completely delivered is generated.

10. The medicament delivery device according to claim 9, wherein the rotational displacement of the delay element in relation to the signal generating element is rotationally damped by a viscous media arranged between the delay element and the signal generating element.

11. The medicament delivery device according to claim 9, wherein said second guide and hold elements comprise guide tracks and a central radially extending protrusion arranged on the outer circumferential surface of said signal generating element and a radial inwardly extending protrusion arranged on the inner circumferential surface of said delay member.

12. The medicament delivery device according to claim 11, wherein the central radially extending protrusion arranged on the outer circumferential surface of said signal generating element comprises an inclined side surface and the radial inwardly extending protrusion arranged on the inner circumferential surface of said delay member comprises an inclination side surface such that said side surfaces configured to promote a rotational displacement of the delay element in relation to the signal generating element.

13. The medicament delivery device according to claim 8, wherein the housing comprises a proximal housing part and a main housing part which are releasably connected to each other.

14. The medicament delivery device according to claim 13, further comprising a biased delivery member shield positioned at least partially and axially movable within the housing, said biased delivery member shield being operably connected to the hold-release mechanism such that when said biased delivery member shield is pressed against a delivery site said hold-release mechanism is actuated.

15. The medicament delivery device according to claim 14, wherein a signal generating element spring is arranged between a proximally directed end wall at the proximal end of the plunger rod driver and a distally directed surface of the circular end plate inside the signal generating element and configured to be compressed during medicament delivery.

16. The medicament delivery device according to claim 15, wherein the medicament delivery member shield is interactively connected to the delay element by a connection configured to allow a rotation the delay element in relation to the signal generating element after the medicament has been delivered and the housing parts are rotated in relation to each other such that when the housing parts are separated the signal generating element is axially displaced towards the proximal end of the device by the force of the signal generating element spring.

17. The medicament delivery device according to claim 16, wherein the medicament delivery member shield comprises elongated ledges on the inner surface of the medicament delivery member shield configured to interact with the radially extending ledges of the delay element.

18. The medicament delivery device according to claim 16, wherein the drive mechanism is configured to be displaceable from the released position to the biased position by pushing on the plunger rod driver with a suitable tool in the distal direction causing the drive element to be tensioned until the locking element grips and holds the plunger rod driver.

19. The medicament delivery device according to claim 18, wherein first guide and hold elements are also configured to allow a rotation of the delay element in relation to the signal generating element when the plunger rod driver is displaced towards the distal end.

20. The medicament delivery device according to claim 8, wherein said first guide and hold elements comprise guide tracks arranged on inner surfaces of longitudinally extending arms of the blocking member and radially extending ledges arranged on the outer surface of the delay element.

* * * * *